United States Patent [19]
Fischetti et al.

[11] Patent Number: 5,707,822
[45] Date of Patent: Jan. 13, 1998

[54] GENE SERUM OPACITY FACTOR

[75] Inventors: Vincent A. Fischetti, W. Hempstead; Jasna Rakonjac; John Robbins, both of New York, all of N.Y.

[73] Assignee: The Rockefeller University, New York, N.Y.

[21] Appl. No.: 294,189

[22] Filed: Aug. 22, 1994

Related U.S. Application Data

[63] Continuation of Ser. No. 115,227, Sep. 1, 1993, abandoned.
[51] Int. Cl.⁶ .................. C12Q 1/34; C12N 9/52; C12N 15/57
[52] U.S. Cl. .............. 435/23; 435/220; 435/252.33; 435/320.1; 536/23.2; 536/24.32
[58] Field of Search ................ 435/220, 320.1, 435/252.33, 23; 536/23.2, 24.32

[56] References Cited

PUBLICATIONS

Martinez, O.V. et al., (1978) J. Gen. Microbiol. 105, 29–38.
Saravani, G.A. et al., (1990) FEMS Microbiol. Letts. 68, 35–40.
Lee, C.C., et al., (1988) Science 239, 1289–1291.
Young, R.A., et al., (1983) Science 222, 778–782.

*Primary Examiner*—Charles L. Patterson, Jr.
*Attorney, Agent, or Firm*—Klauber & Jackson

[57] ABSTRACT

Methods and compositions are provided for cloning and expression of serum opacity factor of *Streptococcus pyogenes* genes. The portion produced by the recombinant DNA techniques described herein may be employed in qualitative and quantitative testing for high density lipoprotein, as a fibronectin binding factor and for the regulation of high density lipoprotein in a mammal. The gene may further be employed as a molecular probe for accurate identification of opacity factors from various strains of *Streptococcus pyogenes*.

19 Claims, 11 Drawing Sheets sot22 ORF

1kb

| Insert | | SOF Activity | Clone |
|---|---|---|---|
|  | 9,000bp | + | LSOF22.4 |
|  | 2,543bp | + | pSOF22.1 |
|  | 2,383bp | − | mpSOF22.1d160 |

```
364  N  P  L  F  P  W  L  P  I  F  N  H  T  N  R  K  A  D  M  I  D  D  V  K  Y  L  L  I  K  W  G  E  K  L  G  I  E  G  L  N  D
     TAACCCACTGTTCCCTGGCTTCCCATCTTTAACCACAACGAATCAGAATGATGATTGATGTTAAGTATCTTATTAAGTGGGGTGAAAAATTAGGATAGAAGGCTAAATGA
         1210        1220        1230        1240        1250        1260        1270        1280        1290        1300        1310        1320
404  L  D  N  T  L  K  L  A  G  A  A  S  G  I  V  G  G  F  L  G  G  S  L  T  E  Y  L  S  L  K  E  Y  Q  S  D  R  L  N  A
     CCTAGATATACACATTAAAATTAGCAGAGCAGCAGTGGAATTGTAGGTGGTTTTTAGTGGAGTGGAGTCTAACGGAGTAGTCTTAGCCTTAAAGAATATCAGTCAGACAGGCTTAATGC
         1330        1340        1350        1360        1370        1380        1390        1400        1410        1420        1430        1440
444  S  Q  F  N  Y  E  R  R  V  G  E  G  Y  Y  Y  H  S  F  S  E  R  K  T  A  E  M  P  N  R  A  L  I  K  K  Q  L  E  G  L  F
     AAGTCAATTAATTATGAAAGACGTGTTGGTGAAGGTATTATTACCATAGTTTTTCTGAAAGGAAAACTGCTGAAATGCCGAACAGAGCACTTATTAAGAAACAATTAGAAGGCCTATT
         1450        1460        1470        1480        1490        1500        1510        1520        1530        1540        1550        1560
484  K  G  K  E  G  K  W  F  K  S  I  L  E  K  L  S  L  T  D  D  Y  Q  K  A  K  E  E  A  I  L  K  V  L  D  Y  F  F  Y  K  R
     TAAGGGAAAAGAAGGTAAATGGTTTAAGTCTATTTGAAAAATTATCACTTACAGATGATTATCAAAAGCAAAAGAAGCTATTTTGAAAGTGCTTGATTACTTCTTTTACAAAAG
         1570        1580        1590        1600        1610        1620        1630        1640        1650        1660        1670        1680
524  D  Y  I  Y  Y  N  H  N  L  S  A  I  A  E  A  K  M  A  Q  Q  E  G  V  T  F  Y  S  V  D  V  T  D  F  N  S  A  S  K  R  A
     AGACTATATATTACTACACAATCACATCTCTACAATCAGCAATCTGAAGCCAAAATGGCTCAACAAGAGGGGTCACCTTCTATTCCGTTGATGTTACTGATTTCAACTCAGCTTCTAAAGACC
         1690        1700        1710        1720        1730        1740        1750        1760        1770        1780        1790        1800
564  K  R  Q  V  K  S  E  E  D  K  K  K  A  K  E  K  E  N  I  E  K  K  R  D  E  K  F  D  N  Y  L  K  Q  M  S  E  G  G  K  E
     AAAGCGACAAGTAAAAGTGAAGAGGATAAGAAGAAAGCAAAAGAGAAGGAAAATATTGAAAAGAAACGTGACGAAAAGTTTGATAATTACTTAAAACAATGTCTGAAGCGGGTAAAGA
         1810        1820        1830        1840        1850        1860        1870        1880        1890        1900        1910        1920
604  F  N  D  V  D  K  A  E  N  F  K  D  T  L  T  S  V  T  V  T  E  T  F  G  N  N  V  S  V  E  S  G  S  W  K  T  S  L  G
     ATTTTTAACGATGTGGATAAGGCCAGAGAATTTCAAAGATACCCTAACCAGTGACAGTGAAGTCTATTTTCACTTGTTCTGTTGAGAGTGGTTCATGGAAAACTTCACTAGG
         1930        1940        1950        1960        1970        1980        1990        2000        2010        2020        2030        2040
644  S  N  S  G  S  S  R  E  V  S  Y  K  G  R  D  S  G  S  L  F  S  L  F  G  S  T  K  E  S  L  T  W  T  I  S  K  D  Q  L
     TAGTAATAGTGGTTCAAGTAGCAGAGAGGTTTCCTATAAAGGACGGGATAGTGGAAGTCTGAAGTCTATTTCGGTAGTACCAAAGAAGTCTCACTTGGACTATTTCCAAAGACCAGTT
         2050        2060        2070        2080        2090        2100        2110        2120        2130        2140        2150        2160
684  K  Q  A  F  E  E  G  K  P  L  T  Y  K  L  V  D  K  D  K  F  R  E  T  L  K  K  Q  Q  E  S  R  R  I  K  K  R  A
     GAAACAAGCCTTTGAAGAGGGTAAGCCGCTAACCCCTACCCTATAAAGCTGAAAGTTGATAAAGTTGATAAAGATAAATTAGAGAGAACTCTTAAAAAGCAACAAGAATCTCGTCGTATAAAGAAACGAGC
         2170        2180        2190        2200        2210        2220        2230        2240        2250        2260        2270        2280
724  A  S  S  E  E  N  T  V  T  E  T  I  I  S  N  K  I  S  Y  K  I  N  N  G  K  D  T  N  N  K  L  E  E  V  K  M  S  Y
     AGCATCTTCGGAAGTGAGAACACTGTCACAGAAACATATTATTTCAAATAAAAGATTCTTACAGATTAAGATAACGAATAAATGGTAAGAAGATAACGAATAACATAATAATGTCTTA
         2290        2300        2310        2320        2330        2340        2350        2360        2370        2380        2390        2400
```

FIG. 4C

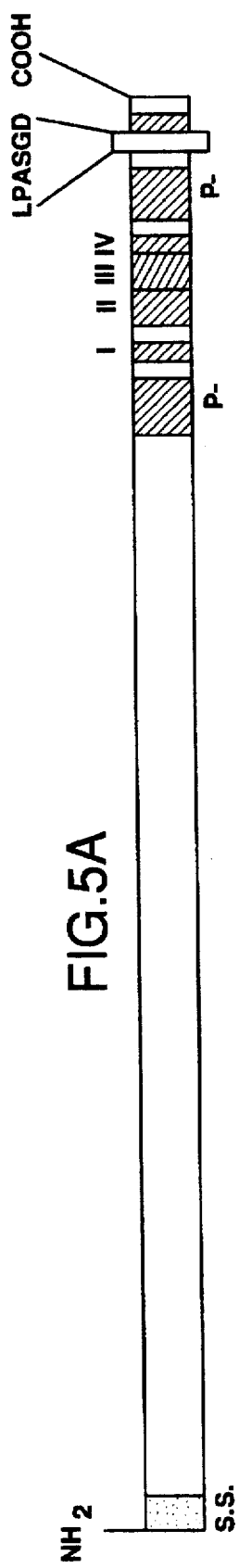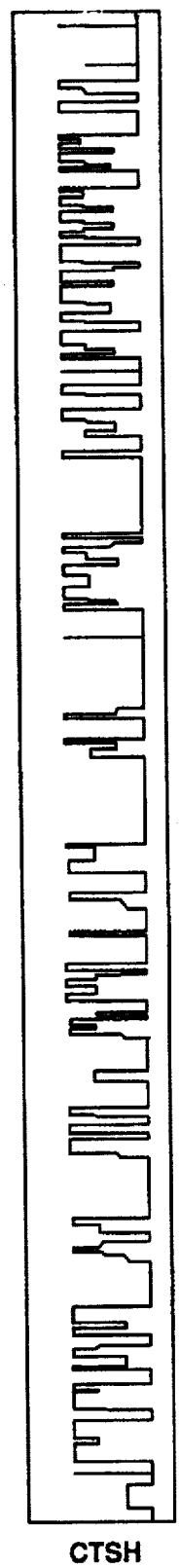
FIG.5A  FIG.5B  FIG.5C

FIG.6

REPEAT REGION OF SOF22 AND ITS RELATIONSHIP TO FIBRONECTIN
BINDING PROTEINS OF GROUP A STREPTOCOCCI AND STAPHYLOCOCCI

| | | |
|---|---|---|
| II | QENKDPIVDITEDTQPGMBGSNDAT | |
| II/III | 869 VVEEDTTPQRPDVLVGGQSDPI-DITEDTQPSMSGSNDAT | |
| III/IV | 908 VVEEDVTPKRPDILVGGQSDPI-DITEDTQPSMSGSNDAT | |
| IV | 947 VIEEDTKPKRFFHFDNE | |

| | | |
|---|---|---|
| SOF22 | 869 VVEEDTTPQRPDVLVGGQSDPIDITEDTQPSMSGSNDAT | 100% |
| Sfb23 | 126 VETEDT-KE-PGVLMGGQSESVEFTKDTQTGMSGQTTPQ | 46% |
| FnBP | 947 IIEEDTNKDKPSYQFGGHN-SVDFEEDTLPKVSGQNEGQ | 38% |

FIG.7

```
SOF22     SLSLPQAPVYKAAHH  LPASGD  KREASFTIVALTIIGMGLLSKKRRDTEEN
M6        KPNQNKAPMKETKRQ  LPSTGE  TANPFFTAAALTVMATAGVMWKR-KEEN
Prot.H    KPNQNKAPMKETKRQ  LPSTGE  TANPFFTAAALTVMATAGVMWKR-KEEN
M49       QANRSRSAMTQQKRT  LPSTGE  TANPFFTAAAATVMVSAGMLAL-KR-KEEN
ML2.2     QTATRPSQNKGMRSQ  LPSTGE  MNPFFTAAAATVMVSAGMLAL-KR-KEEN
Prot.G    KKPEAKKDDAKKAET  LPTTGE  GSNPFFTMALAVMAGAGALAVASKRKED
WAPA      TTTSKQVTKQKAKFV  LPSTGE  QAGLLLTTVGLVIVAVAGVYFYRTRR
Prot.A    KKQPANHADANKAQA  LPETGE  ENPLIGTTVFGGLSLALGMLLAGRRREL
FNBP      KAVAPTKKPQSKKSE  LPETGG  EESTNKGMLFGGLFSILGLALLRRNKKNHKA
SCP       SSKRALATKASTRDQ  LPTTND  KDTNRLHLLKLVMTTFFFGLVAHIFKTKRQKETKK
Sfb       VEENREKPTKNITPI  LPATGD  DIENVLAFLGILILSVLPIFSLLKKQTKQ
SOF22     SLSLPQAPVYKAAHH  LPASGD  KREASFTIVALTIIGMGLLSKKRRDTEEN
```

FIG.8

```
sof22  GATCATTAATTTTTATCTCTCACCAAAAACTGA-TTTTAGAAACGAAAAAGCATGGTGTATATAAAGTTC
         -|||  ||      ||||||      |||| |||||    ||         ||||||||||||||
scpA   AGTCACAAACTAAACAACTCTTAAAAGCTGACCTTTACTAATAATCGTCTTTTTTTATAATAAAGATG
         -70                    -50                -35                    -10
```

GENE SERUM OPACITY FACTOR

This application is an continuation application Ser. No. 08/115,227, Filed: Sept. 1, 1993 now abandoned.

This invention was made with Government support under Grant AI 11822 awarded by the National Institutes of Health. The Government has certain rights in the invention.

FIELD OF THE INVENTION

This invention relates to composition and processes for use as diagnostics for qualitative and quantitative testing for high density lipoprotein (HDL) in body fluids. It relates also to DNA sequences for the production of polypeptides useful for such purposes because of the apolipoproteinase activity (ALA) of such polypeptides.

Apolipoproteins are particles in the blood that are intimately involved in coronary heart disease. They are amalgams of proteins, cholesterol and lipids that appear to be the principal factors participating in the transportation and deposition of cholesterol in human blood. The most abundant of the apolipoproteins are low density lipoprotein (LDL) and HDL, LDL appears to be principally responsible for the deposition of cholesterol in arterial plaque. In contrast, HDL appears to be principally responsible for transportation of cholesterol to the liver for metabolism and elimination. These contrasting mechanisms account for the association of increased risk of coronary disease with high LDL levels and low HDL levels.

It has been observed that lipoprotein levels can be modified by diet and exercise so as to increase the relative proportion of HDL in human blood. It is, therefore, important to provide the diagnostic capability of determining the level of HDL in human blood both qualitatively and quantitatively.

Opacity factor (OF) is a product of *Streptococcus pyogenes* which is associated with the generation of opalescence of serum. This promotion of opacity in mammalian sera is associated with the ALA of a surface protein of *S. pyogenes* strains by which a substantial fraction of apoprotein A1 is cleaved from HDL leading to coagulation of the remaining fraction with resulting opalescence. This observation makes it apparent that OF would be a useful tool for qualitatively determining the concentration of HDL in mammalian sera. Unfortunately however, the protein responsible for ALA has not been available in sufficient quantitities and purity to permit the development and use of such a test.

The present invention utilizes recombinant DNA techniques to produce DNA sequences which can be introduced into a cloning vehicle such as a phage or a plasmid (which is subsequently employed to transform a host cell such as *E. coli*) to enable the expression of OF, or segments of OF, having ALA activity. The polypeptides thus produced are then isolated, purified and, if desired modified, for example, by labeling, for use in detecting HDL qualitatively and/or quantitatively in mammalian sera.

Recombinant DNA technology involves the technique of DNA cloning whereby a specific DNA fragment is inserted into a genetic element called a vector which is capable of replication and transcription in the host cell. The vector can be either a plasmid or a virus. Plasmids are small, circular molecules of double-stranded DNA that occur naturally in both bacteria and yeast, where they replicate as independent units as the host cell proliferates. These plasmids generally account for only a small fraction of the total host cell DNA, and often carry genes that confer resistance to antibiotics. These genes, and the relatively small size of the plasmid DNA, are exploited in recombinant DNA technology.

The inserted DNA fragment of a recombinant DNA molecule may be derived from an organism which does not exchange information in nature with the host organism, and may be wholly or partially synthetically made. Construction of recombinant DNA molecules using restriction enzymes and ligation methods to produce recombinant plasmids has been described in U.S. Pat. No. 4,237,224, issued to Cohen and Boyer. The recombinant plasmids thus produced are introduced and replicated in unicellular organisms by means of transformation. Because of the general applicability of the techniques described therein, U.S. Pat. No. 4,237,224 is hereby incorporated by reference into the present specification.

A different method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors.

Because it is supercoiled, plasmid DNA can easily be separated from the DNA of the host cell and purified. For use as cloning vectors, such purified plasmid DNA molecules are cut with a restriction nuclease and then annealed to the DNA fragment that is to be cloned. The hybrid plasmid DNA molecules produced are then reintroduced into bacteria that have been made transiently permeable to macromolecules (competent). Only some of the treated cells will take up a plasmid and these cells can be selected for the antibiotic resistance conferred on them by the plasmid since they alone will grow in the presence of antibiotic. As these bacteria divide, the plasmid also replicates to produce a large number of copies of the original DNA fragment. At the end of the period of proliferation, the hybrid plasmid DNA molecules are purified and the copies of the original DNA fragments are excised by a second treatment with the same endonuclease.

Regardless of the method used for construction, the recombinant DNA molecule must be compatible with the host cell, i.e., capable of autonomous replication in the host cell. The recombinant DNA molecule should also have a marker function which allows the selection of host cells transformed by the recombinant DNA molecule. In addition, if all of the proper replication, transcription and translation signals are correctly arranged on the plasmid, the foreign gene will be properly expressed in the transformed cells and their progeny.

BRIEF SUMMARY OF THE INVENTION

Methods and compositions are provided for the cloning and expression of DNA sequences comprising the gene for the OF and segments thereof having ALA in single cell organisms. Also described are methods of culturing these novel single cell organisms to produce OF and polypeptides having ALA as well as methods of identifying such gene products. Still further, the invention comprises the use of the products expressed by such genes to detect HDL qualitatively and/or quantitively. The methods and compositions of the invention are also useful for detecting streptococcal infection by streptococcal strains that produce opalescence, for the regulation of HDL, and fibronectin binding activity.

BRIEF DESCRIPTION OF THE FIGURES

The present invention may be more fully understood by reference to the following detailed description of the invention and the figures in which:

FIG. 4 (SEQ ID NO:2) Nucleotide sequence of sof22 gene from strain D734 and flanking regions. Underlined—putative promotor boxes (−35, −10) and ribosome binding site (r.b.s.). Also underlined are the restriction sites: XhoI, SacI, PstI, Sau3A$_{2543}$ (the end of Sau3A clone), proline-rich regions, and LPASGD (SEQ ID NO:3) sequence. The arrows above DNA sequence (3193-3208)—putative transcription termination signal; asterisk—stop codon, vertical arrow—putative signal sequence cleavage site; R1, R2, R3, R4—repeats.

FIG. 5 Block diagram of SOF22 protein. Symbols: S.S.—signal sequence; P—proline-rich region; I, II, III, IV—repeats; LPASGD (SEQ ID NO:3)—SPXTGX (SEQ ID NO:4) motif. Boxes: black—hydrophobic sequences hatched boxes—repeated sequences; white boxes—unique sequences. b. Secondary structure prediction. T—turn, C—coil H—helix, E—extended. Four levels of line in the plot correspond to the highest of four likelihoods for each residue to be in the indicated secondary structure. c. Relative hydropathy of SOF22. Hydrophobic domains are located above the central line, and hydrophilic domains are below. The x axis represents the amino acid number of the SOF22 sequence.

FIG. 6 (SEQ ID NOS:5–8) SOF22 repeats. A. Repeats of SOF22 are aligned and residues that are the same in the two or more repeats in bold. Dashes—gaps introduced for the alignment purpose. B. Alignment of SOF22 repeat unit with repeats from gram-positive fibronectin-binding repeats. Numbers of subscript: the position of repeats in the respective amino acid sequences; percentile numbers—percent identity with the SOF22 repeat.

FIG. 7(SEQ ID NOS:9–19) Comparison of the C-terminal end of the deduced amino acid sequence of the SOF22 protein with the C terminal region of the surface proteins from gram-positive bacteria. M6—M6 protein from Streptococcus pyogenes, Prot. H—protein H, M49—M49 protein from Streptococcus pyogenes, m2.2—m2.2 protein from Streptococcus pyogenes, SCP—Carboxypeptidase from Streptococcus pyogenes and Prot. G—protein G from group G streptococci. Also shown are: WapA—wall-associated protein A from Streptococcus mutans and Prot A—Protein A and FnBP—fibronectin-binding protein from Staphilococcus aureus. The LPXTGX motif is separated from the rest of the sequence with a space. Bold indicates residues which are conserved in SOF22 and at least one of the proteins aligned. Conservative replacement of T with S in the LPXTGX motif of sof22 is underlined.

FIG. 8 (SEQ ID NOS:20–21) Alignment of promoter regions of scpA and sof22. The 5' noncoding sequences of scpA and sof22 were compared manually, introducing gaps to increase the overlapping of common motifs. Dashes represent gaps. Putative −35 and −10 boxes and VirR elements are underlined.

DETAILED DESCRIPTION OF THE INVENTION

Figure 1:
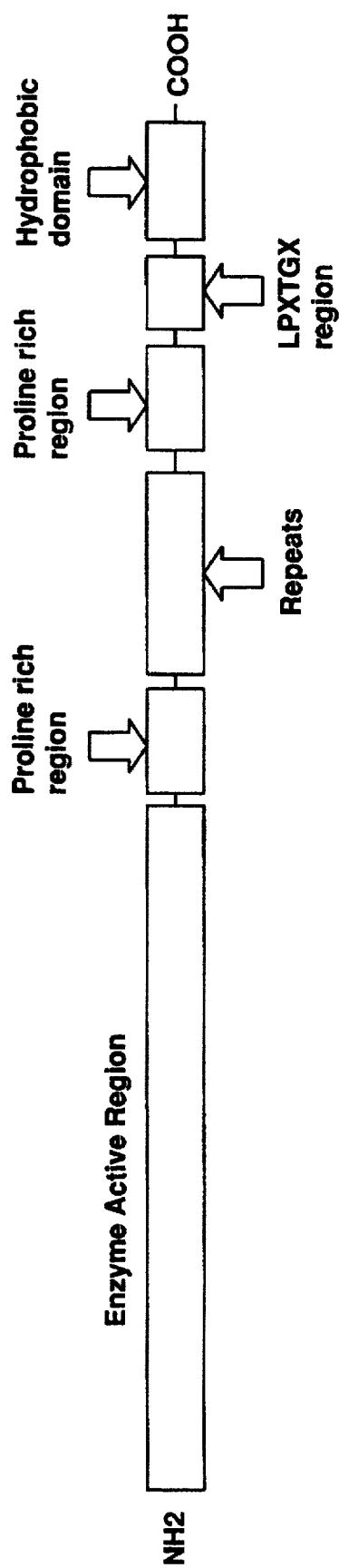
FIG. 1 (SEQ ID NO:1) is a sketch showing the general structure of the polypeptide comprising the OF expressed by a DNA sequence of this invention.

FIG. 1 which is not to scale is a sketch showing the general structure of OF proteins first isolated and made available in useful highly purified form in accordance with this invention. The skilled artisan will recognize the similarity in structure between this surface protein and the antiphagocytic M protein of Streptococcus pyogenes.

As shown, and more fully explained below, it is a protein of 1025 residues expressed by a gene having 3107 base pairs with a molecular weight of about 112,000. The protein has a leader sequence at the amino end which is released as the protein becomes bound to the streptococcal surface. The amino end as shown below is the enzyme active segment of the molecule. While there is serological variation among SOF from different strains, sufficient homology amongst enzyme active segments from different strains exists so that it is possible to utilize the gene, or gene segment, which expresses the enzyme active segment of one strain as a probe to locate the gene which expresses the enzyme active segment of another strain. Each OF therefore has at least one apolipoproteinase segment located at amino end of the molecule.

The OF also includes the hexameric LPXTGX (SEQ ID NO:1) motif characteristic of gram positive bacteria as well as 4 repeats flanked by proline rich stretches within its C-terminal domain. Deletion analysis, as shown below, has been used to establish that the C-terminal domain is not involved in the apolipoproteinase activity of the protein. The repeats are the site of the fibronectin binding activity.

The protein shown in FIG. 1 is representative of the class of OF proteins each having apolipoproteinase activity and isolatable from various streptococcal species. Although there is significant homology amongst the proteins from the various strains, there is also appreciable variation.

There follows a description of the production and isolation of the DNA sequence which expresses the OF of the streptococcal strain D734. The OF protein expressed in this representative example is identified as SOF22. The gene used to express the protein is SOF22. This is in accordance with the standard nomenclature system used in this art. Related testing, cloning, subcloning, expression and probing procedures are also described.

MATERIALS AND METHODS

Bacterial strains, plasmids and bacteriophages. Group A streptococcal strain D734 (M type 22), was the original parent strain of the gene, sof22, described in this study. This strain and all other group A streptococcal strains used in this study were from the Rockefeller University collection and are described in Table 1. *E. coli* strain P2392 served as the host for lambda phage EMBL1. XL1-BLUE (Stratagene Cloning Systems, La Jolla, Calif.) was the host strain for M13 mp18/19, and plasmid pUC9.2 and pBluescript SK$^+$. These two *E. coli* strains did not create an opacity reaction when incubated with heat-inactivated horse serum. The strains and the lambda phage are known and readily available.

TABLE 1

DNA hybridization with mpSOF89.2 probe.

| STRAIN | M-TYPE | CLASS | HYBRID | BANDS | SOR |
|---|---|---|---|---|---|
| D734 | 22 | II | + | 1.60 | + |
| B234 | 22 | | + | 3.50, 0.60 | + |
| B401 | 22 | | + | 3.50, 0.60 | + |
| F312 | 22 | | + | 3.50, 0.60 | + |
| B344 | 2 | | + | 1.70 | + |
| B512 | 4 | | + | 1.60, 0.35 | + |
| D691 | 11 | | + | 1.20, 0.23, 0.20 | + |
| D474 | 13 | | + | 1.60 | + |
| D742 | 13 | | + | 2.50, 0.90 | + |
| B737 | 49 | | + | 0.40 | + |
| D976 | 51 | | + | 0.80, 0.60, 0.23 | + |
| D398 | 60 | | + | 0.18 | + |
| A956 | 62 | | + | 0.22 | + |
| D459 | 63 | | + | 0.22 | + |
| D794 | 66 | | + | 0.23 | + |
| D710 | 1 | I | − | | − |
| B788 | 5 | | − | | − |
| D471 | 6 | | − | | − |
| S43 | 6 | | + | 0.80, 0.60, 0.23 | − |
| A374 | 12 | | + | 1.90 | − |
| D469 | 12 | | − | | − |
| 1RP284 | 24 | | − | | − |
| D617 | 30 | | − | | − |
| D466 | 37 | | − | | − |
| D421 | 41 | | + | 1.90, 0.23 | − |
| D463 | 41 | | − | | − |
| D432 | 54 | | − | | − |
| D442 | 55 | | − | | − |
| D735 | NT* | | − | | − |
| D739 | NT* | | − | | − |

Chemicals and enzymes. Restriction and T4 DNA ligase were purchased from New England BioLabs, Inc. (Beverly, Mass.). Alkaline phosphatase (from calf intestine), human fibronectin and Random primed DNA labeling kits were obtained from Boehringer Mannheim Corp. (Indianapolis, Ind.). DNA sequences were determined by using Sequenase version 2.0 kits (United States Biochemical Corp. Cleveland, Ohio.). Unidirectional deletions of M13mp18/19 clones were generated using the Cyclone 1 Biosystem (International Biotechnologies, Inc, New Haven, Conn.). Na$^{125}$I and radionucleotides [−$^{32}$P]dATP and [−$^{35}$S]dATP were obtained from New England Nuclear (Boston, Mass.). DNA oligomers were purchased from Operon Technologies (Alameda, Calif.), or United States Biochemical Corp. Polymerase chain reactions (PCR) were achieved using the GeneAmp PCR reagent kit (The Perkin-Elmer Corp., Norwalk, Conn.). Heat-inactivated horse serum was purchased from Life Technologies, Inc. (Gaithersburg, Md.). All other chemicals were purchased from Sigma Chemical Co. (St. Louis, Mo.), unless otherwise indicated.

Serum Opacity Reaction Assays

OF expressed by colonies of strain D734 was detected by growing bacteria on serum opacity reaction (SOR) assay medium, containing 50% heat-inactivated horse serum and Todd Hewitt broth (Difco Laboratories, Detroit, Mich.) in 0.9% Oxoid Ion agar No. 2 (Colab Laboratories, Chicago Heights, Ill.). Recombinant phage plaques expressing OF activity were screened on plates containing Luria broth instead of Todd Hewitt broth. After transferring phage lawns to nitrocellulose filters, the OF-positive plaques were detected by replica plating the filters on SOR assay medium for 10–12 h at 37° C. Serum opacity activity in solutions, including supernatants of phage or bacterial cultures, was measured as previously described. Briefly, the liquid solution to be tested was mixed 1:5 in heat-inactivited horse serum, containing 0.02% merthiolate, and incubated for 2 h at 37° C. Opacity was quantitated by spectrophotometric measurement at 475 nm.

To visualize OF protein bands after denaturing SDS-PAGE electrophoresis, the gel (10%) was incubated on solid SOR assay medium containing 0.02% merthiolate. Of protein was detected as opaque bands in the SOR assay medium and photographed under indirect light.

Extraction of OF From Streptococci

Late log phase cultures of strain D734 were washed with 200 mM sodium phosphate buffer, pH 7.5, at 4° C. and resuspended in 1/100 of the original culture volume of the same buffer. Extraction of OF proceeded by incubating the bacterial suspension of 2 hours at 37° C., followed by centrifugation and filtration of the resulting supernatant through a 0.45 um nitrocellulose filter (Schleicher and Schuell, Inc., Keene, N.H.). OF was precipitated from the supernatant in 60% saturated ammonium sulfate and collected by centrifugation (31,500 g×10 min.). The precipitate was resuspended in 100 mM Tris-HCl, pH 7.5, and dialyzed in 4 liters of the same buffer for 48 hours at 4° C.

Cloning Procedures

Streptococcus chromosomal DNA for all work was prepared by the known phage lysin extraction procedure.

Chromosomal DNA from strain D734, used in creating recombinant libraries, was either partially digested with Sau3AI, or completely digested with EcoRI. Sau3AI digest was dephosphorylated with calf intestinal phosphatase, and ligated to lambda phage EMBL4 arms digested with BamHI and SalI. The EcoRI digest was ligated to dephosphorylated EMBL4 arms prepared by BamHI and EcoRI cleavage. Ligation mixtures were packaged in vitro using Gigapack II gold packaging extracts (Stratagene).

Unamplified libraries were plated on strain P2392 and screened for recombinant phage plaques expressing an OF phenotype. Four positive phage (LSOF22.1–LSOF22.3 and LSOF22.4 from the Sau3A and EcoRI libraries, respectively) were isolated and plaque purified.

Subcloning Procedures

For OF expression studies and DNA sequencing of the 5' portion of sof22, a 2,560 bp EcoRI-SalI fragment, containing the entire 2,543 bp insert of phage LSOF22.3, was electrophoretioally purified and than ligated to both M13 mp18 and mp19 digested with both EcoRI and SalI, creating mpSOF22.2 and mpSOF22.1, respectively. Ligation mixtures used to transform XL1-Blue yielded numerous recombinant plaques, as detected by plating on SOR assay agar. Sets of nested deletion clones for DNA sequencing were then prepared from both M13 clones using the Cyclone I kit (IBI). To sequence the 3' portion of sof22, an 3,100 bp SacI-EcoRI (FIG. 3) fragment was subcloned from LSOF22.4 into both M13 mp18 and mp19, creating mpSOF22.4 and mpSOF22.3, respectively. The 2543 bp insert of phage LSOF22.3 was also cloned into pBluescript KS$^+$ (pSOF22.1).

DNA Sequence and Sequence Analysis

Single stranded templates of M13 and mp18/19 clones were prepared for chain termination sequencing by known methods. DNA sequences of mpSOF22.1 and mpSOF22.2 derived deletion clones were determined using the M13-20 forward universal primer, Sequenase 2.0, and [-$^{35}$P]dATp. The 3' portion of sof22, cloned in mpSOF22.3 and mpSOF22.4, was sequenced by primer walking.

DNA sequence data was aligned using the STADEN program package (Roger Staden, MRC Laboratory of Molecular Biology, Cambridge, U.K.). This software package was also used to predict structural features of the deduced OF protein. The Genbank database was accessed to establish regions of homology between SOF22 and other known proteins.

Subcloning of the Fibronectin Binding Domain (FNBD22)

The RF form of mpSOF22.3 served as the template for amplification of the FNBD of sof22. The 5' primer,(SEQ ID NO:23) CCC<u>AAGCTT</u>CAGGAAAATAAAGAT, designed to place the FNBD coding sequence in frame with the upstream lacZ gene fragment, corresponded to bases 2641 to 2658 (FIG. 4) and a HindIII site (underlined), while the 3'primer, (SEQ ID NO:23) CG <u>GGATCC</u>GCTCGTTATCAAAGTGG, consisted of nucleotides 3002 to 2986 (FIG. 4) and a BamHI site. The PCR reaction consisted of 20 cyles of a three step reaction (1 min at 94° C., 3 min at 55° C., and 3 min at 72° C.), employing the GeneAmp PCR reagent kit, native TaqDNA polymerase, and a DNA Thermal Cycler (The Perkin-Elmer Corp.). The products, of expected size, from 3 independent PCRs, were pooled, purified by phenol/chloroform extraction, digested with HindIII and BamHI, and isolated from a low melting temperature agarose gel. Purified DNA was then ligated to the HindIII and BamHI sites of pUC9.2, creating the FNBD expressing clone, pFNBD22.1.

Fibronectin Binding Studies

The recombinant fibronectin binding domain was prepared from the whole cell lysates of clone pFNBD22.1, separated by denaturing SDS-PAGE and electroblotted to nitrocellulose. The blots were then blocked by incubation in 10 mM HEPES buffer, containing 150 mM NaCl, 10 10 mM MgCl$_2$, 2 mM CaCl$_2$, 50 mM KCl, 0.5% Tween-20, 0.04% NaN$_3$, and 0.5% BSA, pH 7.4, for 2–3 h at room temperature. Subsequently, blots were then probed for 3–4 h at room temperature in the same buffer containing $^{125}$I fibronectin adjusted to 3×10$^5$ cpm/ml. Blots were then washed three times with blocking buffer, dried and exposed to Kodak Blue Brand film in the presence of an intensifying screen, for 24–36 h, at −70° C.

Radioiodination of fibronectin was achieved using Iodobeads (Pierce Chemical Cl., Rockford, Ill.). The labeled protein was separated from free iodine by filtration through Sephadex G-25 (PD-10; Pharmacia LKB Biotechnology Inc.) and collected in 100 mM phosphate buffer saline, pH 6.5. The specific activity of the iodinated fibronectin was ×10$^6$ cpm/ug.

ApoAI Cleavage Assay

Crude lysates of clones LSOF22.3 or EMBL4 were mixed with purified human HDL in microtiter plate wells and incubated for 16 h at 37° C. in the presence of 0.02% NaN$_3$-HDL was adjusted to a final apoprotein concentration of 30 ug/100 lysate. When included in the reaction, aspartic protease inhibitor pepstain A (5 ug/ml) was incubated with lambda lysates for 30 min prior to the addition of HDL. Opacity reactions were assessed by observation in indirect light. Cleavage of ApoAI was analyzed by denaturing SDS-PAGE observation in indirect light. Cleavage of ApoAI was analyzed by denaturing SDS-PAGE (15) of 10 ul of each reaction. Electroblotted filters were probed with alkaline phosphatase-conjugated sheep anti-ApoAI antibody (Biodesign International, Kennebunkport, Me.) and developed.

DNA Hybridization

Chromosomal DNA prepared from streptococci was digested to completion with restriction enzymes and electrophoresed in 0.6% or 1.05% agarose gels prior to transfer to Hybond membranes (New England Nuclear). DNA probes, consisting of either restriction fragments or PCR products, were isolated from preparative low melting temperature agarose gels and then radiolabeled with [$^{32}$P]dATP, using random primed DNA labelling kits (Boehringer Mannheim Corp.).

Figure 4A:
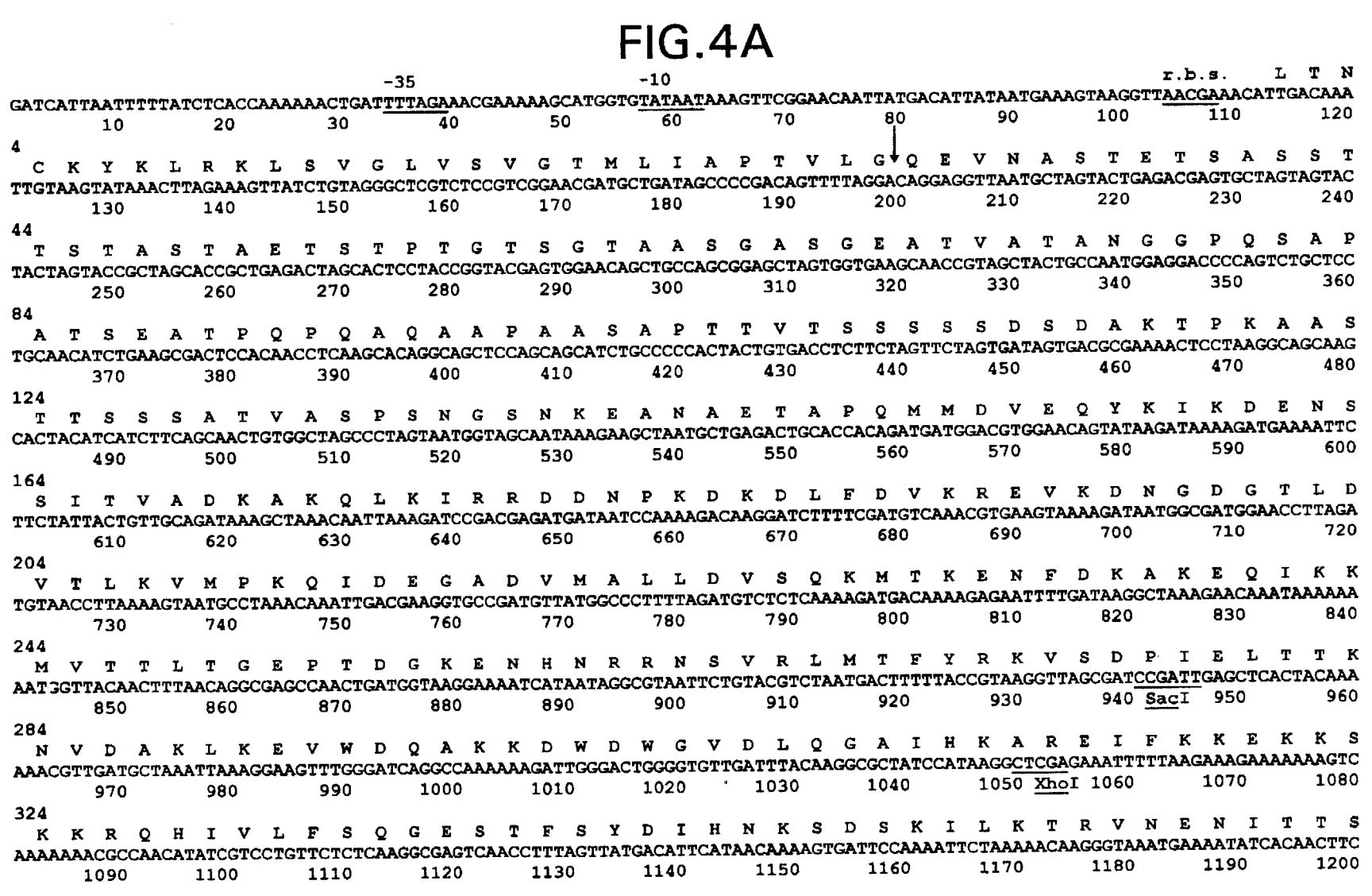
Figure 4C:
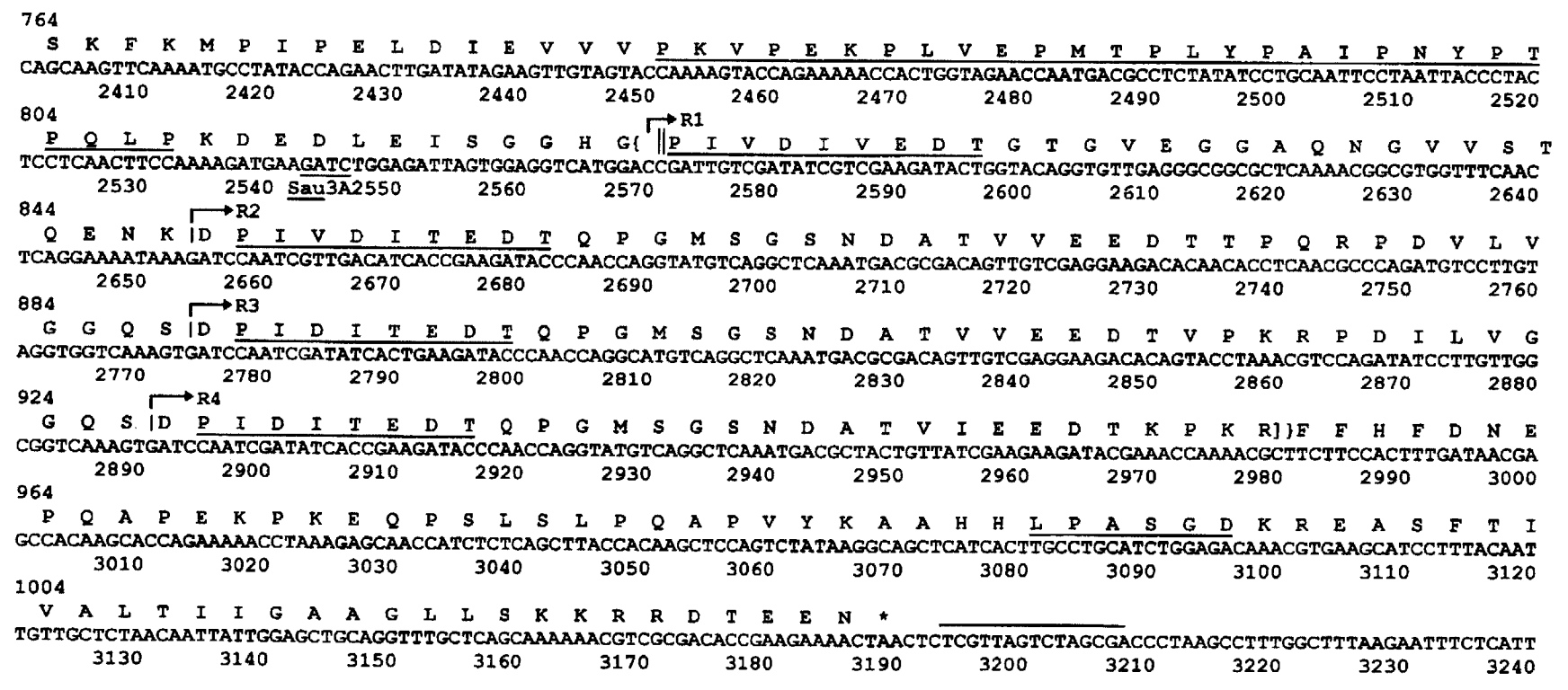

Blots were incubated in a prehybridization solution (6× SSC, 0.5% SDS, 100 ug/ml denatured salmon sperm DNA, 5× Denhardt's solution and 50% formamide), at 30° C. overnight, and then hybridized with radiolabeled probes in a hydrization solution (6× SSC, 0.5% SDS, 100 ug/ml denatured salmon sperm DNA and 50% formamide), at 42° C. overnight in accordance with known procedures. Blots that physically mapped the sof22 and emm2 loci were washed at high stringency conditions that allowed for less than 5% bp mismatch (twice in 0.1% SSC and 0.1% SDS for 30 min at 65° C.). Probes used for restriction mapping of sof22 were inserts from M13 deletion clones mpSOF22.81 and mpSOF22.792, corresponding to nucleotides 1 to 781 and 1,160 to 2,543, respectively (FIG. 4). Blots detecting sof22 homologs in other group A streptococcal strains were sequentially washed at both high and low stringency conditions. Whereas high stringency washes allowed for less than 5% mismatched, relaxed wash conditions (twice in 0.2% SSC and 0.5% SDS for 30 min at 37° C.) allowed up to 20% mismatch. The probe in these experiments was the insert from the M13 clone mpSOF22.692, corresponding to an internal Sau3A fragment (bp 976 to 2,543) encoding the serum opacity domain (SOD).

RESULTS

Extraction of Serum Opacity Activity From Streptococcus pyogenes

Figure 2:
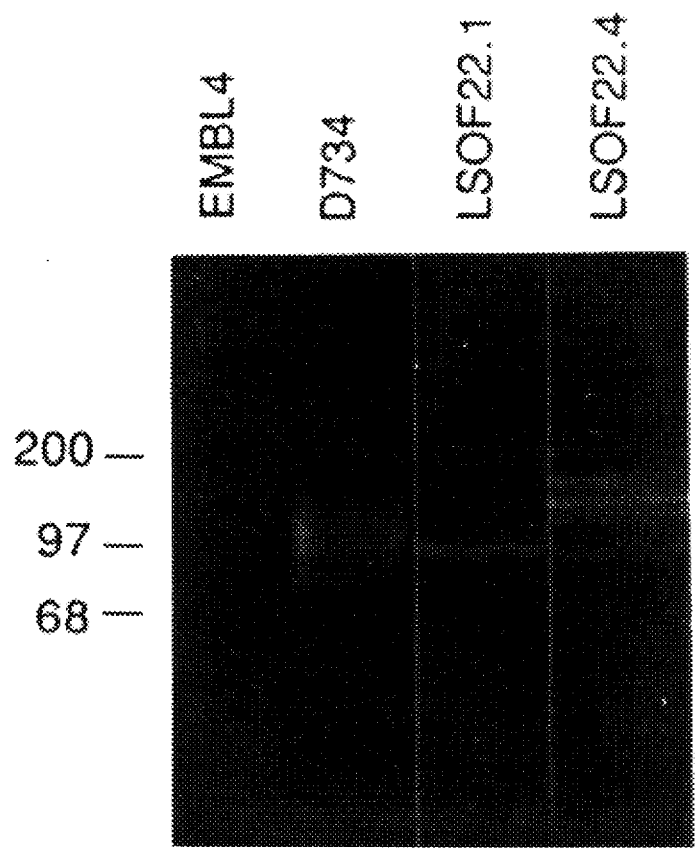
FIG. 2 SOR (overlay) assay of SOF22 protein from strain 22 streptococcus D734 and recombinant phage lysates. D734—released from of SOF22 PROTEIN FROM STREPTOCOCCAL STRAIN d734. RECOMBINANT PHAGE LYSATES: lsof22.3—sAU3a CLONE, 2456 BP INSERT; lsof22.4—ECoRI clone, 9 kb fragment containing the whole sof22 open reading frame; EMBL4—vector lysate. Recombinant phage crude lysate was directly loaded on the gel. Molecular weight standards (in kD) are indicated.

The serum opacity factor of group A streptococci can be detected in both extracellular and membrane bound fractions isolated from bacterial cell cultures. To both ascribe the basis of the serum opacity reaction to a specific molecule(s) and judge the feasibility of molecularly cloning the serum opacity factor, a maximum yield method to extracting the released form of the factor was established as described above. The protein extract of SOF-producing strain D734 was analyzed by SDS-PAGE under denaturing conditions and used in a serum opacity reaction assay. As can be seen in FIG. 2, these methods isolated and detected at least two closely migrating species, with molecular weights of 100 kD that are capable of independently producing a serum opacity reaction. Thus, a simple and dependable assay capable of detecting molecules responsible for a serum opacity reaction was established.

Cloning of sof22

Two streptococcus genomic libraries, containing either Sau3AI or EcoRI restriction fragments of strain D734 chromosomal DNA, were constructed in EMBL4 vector and screened for recombinant phage clones exhibiting a serum opacity phenotype. For the detection of SOF protein expression in phage plaques, the method described above was employed. By assaying for positive plaques in this manner, four phages, SOF22.1 to SOF22.3 from the Sau3AI library and SOF22.4 from the EcoRI library, were identified, isolated,and confirmed as serum opacity producing phages.

Crude phage lysates of clones SOF22.1 to SOF22.3 were all found to contain a protein with serum opacity activity that corresponds in size, 100 kDa, with the streptococcal serum opacity factor (FIG. 2). In contrast, phage SOF22.4 expressed at least four different molecular species, ranging from 100 kDa to 175 kDa in size, with serum opacity activity (FIG. 2).

Figures 3A, 3B:
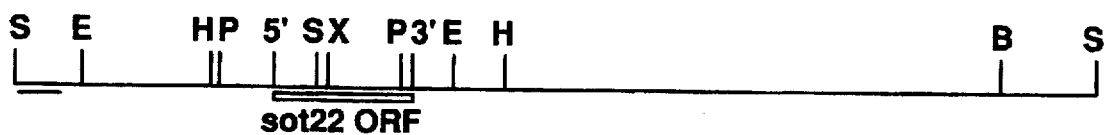
FIG. 3 Restriction map of sof22 locus and surrounding region on the chromosome of D734.A. Bar denotes the sof22 open reading frame (ORF). 5', 3'-termini of sof22 ORF.B-BamHI; E-EcoRI; H-HindIII; P-PstI; S-SacI; X-XhoI. B. Determination of N-terminal consensus required for SOF activity. Bars represent sof22 ORF fragments in the two deletion clones, aligned with the restriction map in A. 2643, 2383—the length of 3'-terminal deletion clones of sof22 ORF in correspondent clones.

The differences in both the number and mobility of the major reactive species of SOF expressed by recombinant clones SOF22.1 to SOF22.3 and SOF22.4 were found to parallel the insert sizes of these clones. All three clones from the Sau3AI library had identical 2.5 kb inserts flanked by EMBL4 linkers and SalI stuffer fragments. Phage SOF22.4 harbored an EcoRI fragment, which contained the Sau3AI cloned in LSOF22.1–LSOF22.3 (FIG. 3). Thus, with codon requirements for the expression of a 100 kD protein in mind (typically 3 kb), it was concluded that phages SOF22.1 to SOF22.3 encode a truncated sof22 gene, and that, minimally, phage SOF22.4 encodes the entire sof22 locus. In that one species of SOF released from streptococci comigrated with the solitary SOF species expressed by SOF22.3, we concluded that at least one form of SOF released from streptococci is smaller than the native cell bound form. These were verified by sequencing subclones of these phages (described below).

Subcloning and Sequencing of sof22

To prepare DNA templates for DNA sequencing, the SOF22.3 phage insert was sublconed in M13mp18 and mp19, creating mpSOF22.2 and mpSOF22.1, respectively. The insert was, therefore, in both orientations relative to the lacZ promoter. SOF was expressed from both recombinant phages. Increased levels of IPTG did not increase the level of periplasmic SOF activity. Thus, it was indicated that sof22 was expressed from its streptococcal promoter in these recombinant phages. Sequence analysis of the 2,543 bp fragment from a set of nested deletion clones derived from mpSOF22.2 and mpSOF22.1 detected an ORF, 2,470 nucleotides long, starting at nucleotide 83 and lacking the stop codon. All other ORFs detected were smaller than 1,500 pb. The 2,470 bp long ORF, (sof22), was the only one corresponding to the size of SOF22 produced by LSOF22.3. The 3' portion of sof22 of ORF was located on a 3,100 bp SacI-EcoRI fragment by hybridization, using a probe homologous to the sequences downstream from a unique SacI$_{941}$ site (FIGS. 3, 4). This 3,100 bp SacI-EcoRI restriction fragment, contained in the EcoRI insert of phage SOF22.4, was subcloned in both M13mp18 and mp 19, and sequenced by primer walking. The 3'end of sof22 ORF was located at nucleotide 3,178,644 bp downstream of the end of 2,543 Sau3A fragment.

Analysis of the sof22 Gene Sequence

The nucleotide sequence of sof22 with its deduced amino acid sequence is shown in FIG. 4. The nucleotide sequence begins at the Sau3A site (position 1) and ends at position 3,240. Restriction sites XhoI, SacI, PstI and one Sau3A (the 3' end of Sau3A LSOF 22.3 insert) are indicated in the figure. sof22 ORF starts at the position 83 and ends at the position 3,187. The longest protein that could be coded for by this ORF starts with the alternate start codon UUG at position 113 and codes for a protein of 1,025 aminoacids with a size 112,735.1, about 10% larger than the largest major SOF band released from D734.

Although there were a few standard (AUG) start codons downstream of proposed UUG codon, none of the deduced protein sequences contained hydrophobic signal sequence that would allow export of SOF from the cytoplasm (FIG. 5C). Position of the signal sequence cleavage site, predicted by the method of Von Heijne, was between $G_{29}$ and $Q_{30}$.

Analysis of the amino acid composition of OF22 protein revealed that the most abundant amino acids were lysine (10.54%), serine (9.27%), threonine (8.29%) and glutamine (8.00%). Secondary structure analysis predicts a protein consisting of 39.3% helix, 28.2% random coils, 18.15% beta sheet and 14.3% turns (FIG. 5B). Consistant with the low helix potential for the molecule, analysis of the sequence employing the "Matcher" algorithm showed no significant seven residue periodicity, excluding the possibility of coiled coil structure. Hydrophaticity analysis by the Kyte and Doolittle algorithm shows strong hydrophobic regions both at the first N-terminal 30 amino acids, in the position of the signal sequence, and at the C terminus, in the position of a possible membrane anchor segment (FIG. 5C). C-terminal to the hydrophobic segment (at the C-terminal end of the protein) are eight charged and two polar amino acids. Three residues N-terminal from the hydrophobic domain is a hexameric LPXTGX (SEQ ID NO:1) motif found in the surface proteins from gram-positive bacteria, with conservative replacement T to S.

Analysis of internal homology by Diagon proportional algorithm showed 4 repeats (FIG. 7). Repeats are flanked by proline rich stretches (FIGS. 5a, 6A). All these motifs are present in the majority of streptococcal surface proteins.

The 214 C-terminal amino acids, including repeats and downstream proline-rich region, are dispensable for serum opacity activity, as concluded from the SOF activity of the truncated SOF22. Further shortening of 2,543 bp Sau3A fragment in clone mpSOF22.1 by the deletion of 60 C-terminal amino acids (180 3' base pairs) abolishes SOF activity (FIG. 2). Therefore, the sequence necessary SOF activity is between amino acid 752 and 811.

Sequence Homology With The Membrane Anchor Region of streptococcal Surface proteins Comparisons of deduced amino acid sequence of the SOF22 protein with a protein sequence database revealed homologies of about 30 to 35% confined primarily to the C terminal region, including the LPXTGX (SEQ ID NO:1) motif, hydrophobic domain and charged tail of streptococcal proteins deduced from DNA sequence. These include ennX and emm49 genes from M type 49, emm6 from M type 6, emm12 from M type 12, emm5 from M type 5, protein G protein H and protein Arp4. Comparison of the anchor region of several surface proteins from the Gram positive bacteria is shown in FIG. 7.

Features of sof22 Upstream Sequences.

Putative promoter region shows significant homology to the scpA promoter. Comparison of the two sequences shown on FIG. 9 yields highest degree of homology in the regions around −10 box and upstream of −35 box including 2 putative VirR binding consensus elements upstream of −35 box.

Homology of sof22 With Other Streptococcal sof Genes

Figure 9A:
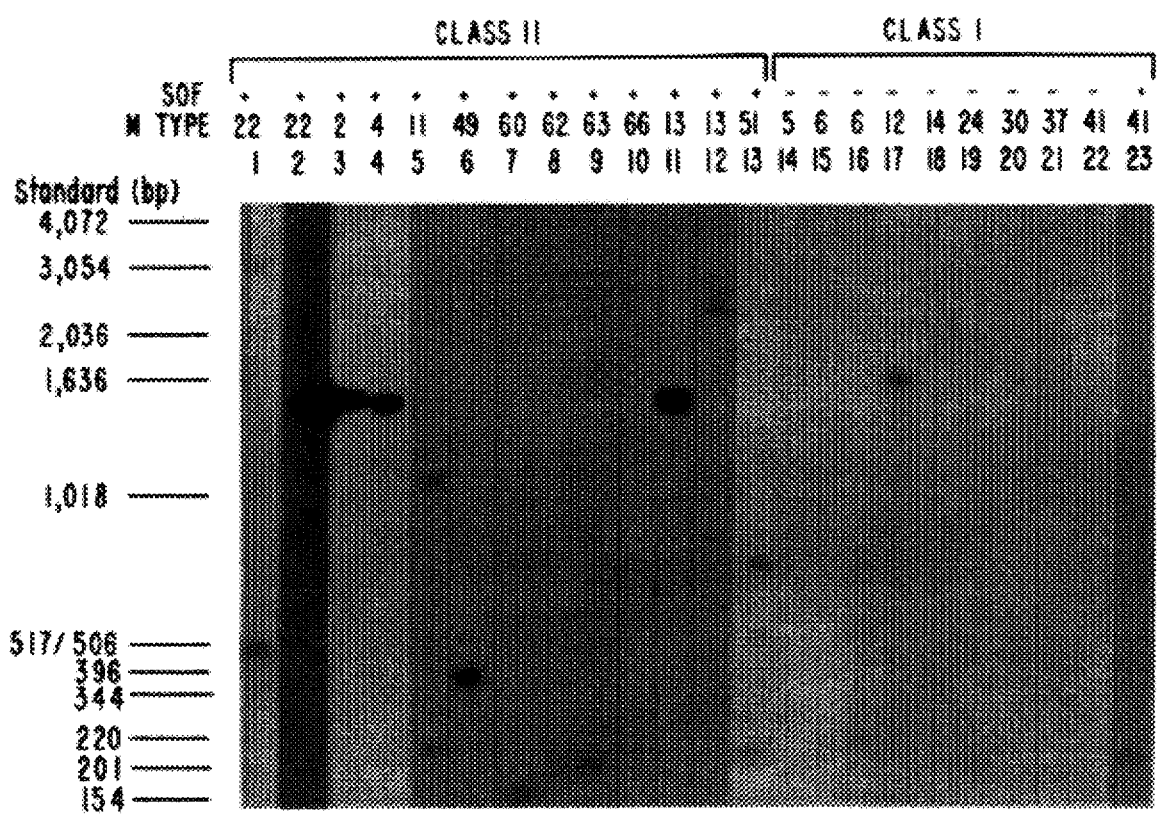
FIG. 9 A. Autoradiogram of Sau3A hybridization patterns of representative streptococcal strains. Washes were done under conditions that allow 20% mismatch. Probe mpSOF69.2 was cloned from M22 strain D734. This probe is homologous to the sof22 intragenic Sau3A fragment spanning from nucleotide 890 to 2543 of the sequence shown in FIG. 3. The exposure of autoradiogram was 10 hrs, with the exception of D734 line which was exposed for 30 min in order to decrease the intensity of the signal. B. The probe and the sau3A map of sof22 locus from strain D734. S—Sau3A restriction site; 5', 3'—margins of sof 22
Figure 9B:
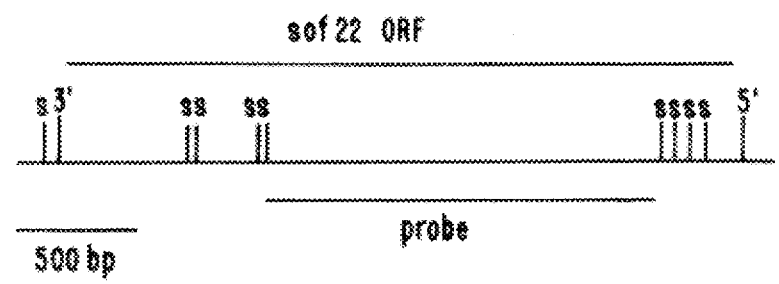

Probe mpSOF69.2 homologous to 1.5 kb long internal Sau3A fragment (nucleotide 890 to 2465) was used for the Southern blot analysis of chromosomal DNA Sau3A digests of 15 OF$^+$ and 15 OF$^−$ strains that belong to different M types (FIG. 9, Table 1). This probe detects the sequence encoding for the functional domain of OF. Under high stringency washing conditions only DNA of strain D734, from which the sof22 gene is cloned, hybridized with the probe. Under relaxed stringency washing (allows 20% mismatch) hybridization patterns obtained with DNAs from non-M22 SOF producing strains were different from that of D734. Unexpectedly, the signals obtained from the strains of the same M types differed among themselves. Both the intensity of the signal and the restriction fragment pattern (length and number) were different for the two strains of M type 13 . Two different patterns were obtained within the M-type 22 strains. 4 M22 strains analyzed fall into the two groups: B243, B401 and F312 in one, and D734 in the other. Out of 15 OF$^−$ strains analyzed one of the 2 M6 strains and a M12 strain gave positive signals. The only class I strain that gave a positive SOF reaction was D421 (M41). It gave a positive signal upon southern hydridization (relaxed conditions). The other M41 strain tested was OF⁻ and showed no signal in the southern blot analysis.

Physical Map Around sof22 Gene And Relation to M Protein

Two probes homologous to the sequences upstream (mpSOF2279.2) and downstream (mpSOF228.1) of the XhoI and SacI sites, were used in Southern blots to construct a physical map around sof22 gene (FIG. 3). Nonoverlapping restriction map was constructed from the autoradiographs obtained after hybridization of an emm22 probe. Calculated from the size of the largest restriction fragments on which sof22 is positioned, its distance from the emm22 gene is at least 30 kbs in the upstream and 15 kbs in the downstream direction.

In FIG. 4, the OF segment is represented by amino acid residues 1 to 1025. The enzymatic active segment is amino acid 1 to 811. The segment 1 to 29 is the leader sequence, LSOF 22.4 and PSOF22.1 identified above have been deposited at the American Type Culture Collection under the numbers ATCC 75541 and ATCC 75542.

What has been described is a cloning and subcloning procedure in which a DNA sequence comprising OF from D734 has been isolated and subcloned to identify the enzyme active segment. The OF of D734 and the enzyme active segment are useful to qualitatively and quantitatively identify HDL by contact with a mammalian fluid suspected of containing it and determining if there has been a reaction. One procedure is to observe the development of opacity qualitatively. The determination can be made quantitative by labeling the protein, for example with a radioactive or enzymatic label and comparing the results with known or preestablished standard curves. The degree of opacity could also be used for quantitation, using a standard curve of known HDL.

The insertion of the selected DNA sequence into a phage or a plasmid to permit the expression of a selected OF or enzyme active segment has also been described.

What is claimed is:

1. A process for producing a polypeptide having apolipoproteinase activity which comprises culturing a prokaryotic unicellular organism containing a recombinant plasmid comprising a DNA sequence coding for said polypeptide and capable of being replicated, transcribed and translated in the unicellular organism, and isolating said polypeptide from the culture, said polypeptide being encoded by a sequence selected from the group consisting of:

(1) the DNA sequences of FIG. 4 (SEQ ID NO. 2);

(2) DNA sequences that hybridize to the DNA sequence of (1) under high stringency hybridization conditions; and (3) DNA sequences that encode an amino acid sequence encoded by the DNA sequences of (1) or (2), and enzyme active segments thereof.

2. A process of claim 1 wherein the DNA sequence is sof22 and codes for SOF22.

3. A process of claim 1 wherein the DNA sequence is SOF22.1 and codes for the fragment of SOF 22 which enzymatically hydrolyzes apoprotein A1 from high density lipoprotein.

4. A process for preparing a prokaryotic unicellular organism having a DNA sequence coding for a polypeptide having apolipoproteinase activity which comprises introducing a recombinant plasmid comprising a DNA sequence coding for said polypeptide and capable of being replicated, transcribed and translated in the unicellular organism, said sequence selected from the group consisting of:

(1) the DNA sequence of FIG. 4 (SEQ ID NO. 2);

(2) DNA sequence that hybridize to the DNA sequence of (1) under high stringency hybridization conditions; and (3) DNA sequences that encode an amino acid sequence encoded by the DNA sequences of (1) or (2), and enzyme active segments thereof.

5. A process of claim 4 wherein the DNA sequence is sof22 and codes for SOF22.

6. A process of claim 4 wherein the DNA sequence is sof22.1 and codes for the fragment of SOF22 which enzymatically hydrolyzes apoprotein A1 from high density lipoprotein.

7. A purified DNA sequence coding for a polypeptide having apolipoproteinase activity, said sequence being selected from the group consisting of:

(1) the DNA sequence of FIG. 4 (SEQ ID NO. 2);

(2) DNA sequence that hybridize to the DNA sequence of (1) under high stringency hybridization conditions; and (3) DNA sequences that encode an amino acid sequence encoded by the DNA sequences of (1) or (2), and enzyme active segments thereof.

8. A purified DNA sequence of claim 7 which codes for SOF22.

9. A purified DNA sequence of claim 7 which codes for the fragment of SOF22 which enzymatically hydrolyzes apoprotein A1 from high density lipoprotein.

10. A cloning vector comprising the DNA sequence of claim 7.

11. A cloning vector of claim 7 which is LSOF22.4 and codes for the production of SOF22.

12. A cloning vector of claim 7 which is pSOF22.1 and codes for the production of the fragment of SOF22 which enzymatically hydrolyzes apoprotein A1 from high density lipoprotein.

13. A unicellular organism containing the vector of claim 10.

14. A unicellular organism containing the cloning vector of claim 11.

15. A unicellular organism containing the cloning vector of claim 12.

16. An *Escherichia coli* bacterium containing the cloning vector of claim 12.

17. A purified DNA probe capable of binding to a DNA sequence coding for a polypeptide having apolipoproteinase activity or any portion of said sequence having such activity, said sequence being selected from the group consisting of:

(1) the DNA sequence of FIG. 4 (SEQ ID NO. 2);

(2) DNA sequence that hybridize to the DNA sequence of (1) under high stringency hybridization conditions; and (3) DNA sequences that encode an amino acid sequence encoded by the DNA sequences of (1) or (2), and enzyme active segments thereof.

18. A diagnostic test for high density lipoprotein in a body fluid which comprises: (a) contacting said body fluid with a polypeptide having apolipoproteinase activity, said polypeptide being encoded by one of the following sequences:

1. the DNA sequence of FIG. 4 (SEQ ID NO:2);

2. DNA sequences that hybridize to the DNA sequences of (1) under high stringency hybridization conditions; and 3. DNA sequences that encode an amino acid sequence encoded by the DNA sequences of (1) or (2);

(b) detecting cleavage of apoprotein A1; and (c) correlating said cleavage with the presence of high density lipoprotein.

19. The test of claim 18 wherein the polypeptide is the enzymatic fragment of SOF 22 which enzymatically hydrolyzes apoprotein A1 from high density lipoprotein.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( v ) FRAGMENT TYPE: C-terminal ( x i ) SEQUENCE DESCRIPTION: SEQ ID NO:1:

```
Leu Pro Xaa Thr Gly Xaa
1               5
```

( 2 ) INFORMATION FOR SEQ ID NO:2:

( i ) SEQUENCE CHARACTERISTICS:
( A ) LENGTH: 3240 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: -35_signal
( B ) LOCATION: 34..39

( i x ) FEATURE:
( A ) NAME/KEY: -10_signal
( B ) LOCATION: 57..62

( i x ) FEATURE:
( A ) NAME/KEY: RBS
( B ) LOCATION: 104..108

( i x ) FEATURE:
( A ) NAME/KEY: CDS
( B ) LOCATION: 113..3190

( x i ) SEQUENCE DESCRIPTION: SEQ ID NO:2:

-continued

```
GATCATTAAT TTTTATCTCA CCAAAAAACT GATTTTAGAA ACGAAAAAGC ATGGTGTATA        60

ATAAAGTTCG GAACAATTAT GACATTATAA TGAAAGTAAG GTTAACGAAA CA TTG          115
                                                          Leu
                                                            1

ACA AAT TGT AAG TAT AAA CTT AGA AAG TTA TCT GTA GGG CTC GTC TCC        163
Thr Asn Cys Lys Tyr Lys Leu Arg Lys Leu Ser Val Gly Leu Val Ser
            5                   10                  15

GTC GGA ACG ATG CTG ATA GCC CCG ACA GTT TTA GGA CAG GAG GTT AAT        211
Val Gly Thr Met Leu Ile Ala Pro Thr Val Leu Gly Gln Glu Val Asn
                20                  25                  30

GCT AGT ACT GAG ACG AGT GCT AGT AGT ACT ACT AGT ACC GCT AGC ACC        259
Ala Ser Thr Glu Thr Ser Ala Ser Ser Thr Thr Ser Thr Ala Ser Thr
        35                  40                  45

GCT GAG ACT AGC ACT CCT ACC GGT ACG AGT GGA ACA GCT GCC AGC GGA        307
Ala Glu Thr Ser Thr Pro Thr Gly Thr Ser Gly Thr Ala Ala Ser Gly
50                  55                  60                  65

GCT AGT GGT GAA GCA ACC GTA GCT ACT GCC AAT GGA GGA CCC CAG TCT        355
Ala Ser Gly Glu Ala Thr Val Ala Thr Ala Asn Gly Gly Pro Gln Ser
                70                  75                  80

GCT CCT GCA ACA TCT GAA GCG ACT CCA CAA CCT CAA GCA CAG GCA GCT        403
Ala Pro Ala Thr Ser Glu Ala Thr Pro Gln Pro Gln Ala Gln Ala Ala
                85                  90                  95

CCA GCA GCA TCT GCC CCC ACT ACT GTG ACC TCT TCT AGT TCT AGT GAT        451
Pro Ala Ala Ser Ala Pro Thr Thr Val Thr Ser Ser Ser Ser Ser Asp
        100                 105                 110

AGT GAC GCG AAA ACT CCT AAG GCA GCA AGC ACT ACA TCA TCT TCA GCA        499
Ser Asp Ala Lys Thr Pro Lys Ala Ala Ser Thr Thr Ser Ser Ser Ala
115                 120                 125

ACT GTG GCT AGC CCT AGT AAT GGT AGC AAT AAA GAA GCT AAT GCT GAG        547
Thr Val Ala Ser Pro Ser Asn Gly Ser Asn Lys Glu Ala Asn Ala Glu
130                 135                 140                 145

ACT GCA CCA CAG ATG ATG GAC GTG GAA CAG TAT AAG ATA AAA GAT GAA        595
Thr Ala Pro Gln Met Met Asp Val Glu Gln Tyr Lys Ile Lys Asp Glu
                150                 155                 160

AAT TCT TCT ATT ACT GTT GCA GAT AAA GCT AAA CAA TTA AAG ATC CGA        643
Asn Ser Ser Ile Thr Val Ala Asp Lys Ala Lys Gln Leu Lys Ile Arg
                165                 170                 175

CGA GAT GAT AAT CCA AAA GAC AAG GAT CTT TTC GAT GTC AAA CGT GAA        691
Arg Asp Asp Asn Pro Lys Asp Lys Asp Leu Phe Asp Val Lys Arg Glu
        180                 185                 190

GTA AAA GAT AAT GGC GAT GGA ACC TTA GAT GTA ACC TTA AAA GTA ATG        739
Val Lys Asp Asn Gly Asp Gly Thr Leu Asp Val Thr Leu Lys Val Met
195                 200                 205

CCT AAA CAA ATT GAC GAA GGT GCC GAT GTT ATG GCC CTT TTA GAT GTC        787
Pro Lys Gln Ile Asp Glu Gly Ala Asp Val Met Ala Leu Leu Asp Val
210                 215                 220                 225

TCT CAA AAG ATG ACA AAA GAG AAT TTT GAT AAG GCT AAA GAA CAA ATA        835
Ser Gln Lys Met Thr Lys Glu Asn Phe Asp Lys Ala Lys Glu Gln Ile
                230                 235                 240

AAA AAA ATG GTT ACA ACT TTA ACA GGC GAG CCA ACT GAT GGT AAG GAA        883
Lys Lys Met Val Thr Thr Leu Thr Gly Glu Pro Thr Asp Gly Lys Glu
        245                 250                 255

AAT CAT AAT AGG CGT AAT TCT GTA CGT CTA ATG ACT TTT TAC CGT AAG        931
Asn His Asn Arg Arg Asn Ser Val Arg Leu Met Thr Phe Tyr Arg Lys
        260                 265                 270

GTT AGC GAT CCG ATT GAG CTC ACT ACA AAA AAC GTT GAT GCT AAA TTA        979
Val Ser Asp Pro Ile Glu Leu Thr Thr Lys Asn Val Asp Ala Lys Leu
275                 280                 285

AAG GAA GTT TGG GAT CAG GCC AAA AAA GAT TGG GAC TGG GGT GTT GAT       1027
```

| | | | | | | | | | | | | | | | |
|---|---|---|---|---|---|---|---|---|---|---|---|---|---|---|---|
| Lys | Glu | Val | Trp | Asp | Gln | Ala | Lys | Lys | Asp | Trp | Asp | Trp | Gly | Val | Asp |
| 290 | | | | | 295 | | | | | 300 | | | | | 305 |

| TTA | CAA | GGC | GCT | ATC | CAT | AAG | GCT | CGA | GAA | ATT | TTT | AAG | AAA | GAA | AAA | 1075 |
|---|---|---|---|---|---|---|---|---|---|---|---|---|---|---|---|---|
| Leu | Gln | Gly | Ala | Ile | His | Lys | Ala | Arg | Glu | Ile | Phe | Lys | Lys | Glu | Lys | |
| | | | | 310 | | | | | 315 | | | | | 320 | | |

| AAG | TCA | AAA | AAA | CGC | CAA | CAT | ATC | GTC | CTG | TTC | TCT | CAA | GGC | GAG | TCA | 1123 |
|---|---|---|---|---|---|---|---|---|---|---|---|---|---|---|---|---|
| Lys | Ser | Lys | Lys | Arg | Gln | His | Ile | Val | Leu | Phe | Ser | Gln | Gly | Glu | Ser | |
| | | | 325 | | | | | 330 | | | | | 335 | | | |

| ACC | TTT | AGT | TAT | GAC | ATT | CAT | AAC | AAA | AGT | GAT | TCC | AAA | ATT | CTA | AAA | 1171 |
|---|---|---|---|---|---|---|---|---|---|---|---|---|---|---|---|---|
| Thr | Phe | Ser | Tyr | Asp | Ile | His | Asn | Lys | Ser | Asp | Ser | Lys | Ile | Leu | Lys | |
| | | | 340 | | | | 345 | | | | | 350 | | | | |

| ACA | AGG | GTA | AAT | GAA | AAT | ATC | ACA | ACT | TCT | AAC | CCA | CTG | TTT | CCC | TGG | 1219 |
|---|---|---|---|---|---|---|---|---|---|---|---|---|---|---|---|---|
| Thr | Arg | Val | Asn | Glu | Asn | Ile | Thr | Thr | Ser | Asn | Pro | Leu | Phe | Pro | Trp | |
| | 355 | | | | | 360 | | | | | 365 | | | | | |

| CTT | CCC | ATC | TTT | AAC | CAT | ACG | AAT | CGT | AAA | GCA | GAC | ATG | ATT | GAT | GAT | 1267 |
|---|---|---|---|---|---|---|---|---|---|---|---|---|---|---|---|---|
| Leu | Pro | Ile | Phe | Asn | His | Thr | Asn | Arg | Lys | Ala | Asp | Met | Ile | Asp | Asp | |
| 370 | | | | | 375 | | | | | 380 | | | | | 385 | |

| GTT | AAG | TAT | CTT | ATT | AAG | TGG | GGT | GAA | AAA | TTA | GGG | ATA | GAA | GGG | CTA | 1315 |
|---|---|---|---|---|---|---|---|---|---|---|---|---|---|---|---|---|
| Val | Lys | Tyr | Leu | Ile | Lys | Trp | Gly | Glu | Lys | Leu | Gly | Ile | Glu | Gly | Leu | |
| | | | | 390 | | | | | 395 | | | | | 400 | | |

| AAT | GAC | CTA | GAT | AAT | ACA | TTA | AAA | TTA | GCA | GGA | GCA | GCT | AGT | GGA | ATT | 1363 |
|---|---|---|---|---|---|---|---|---|---|---|---|---|---|---|---|---|
| Asn | Asp | Leu | Asp | Asn | Thr | Leu | Lys | Leu | Ala | Gly | Ala | Ala | Ser | Gly | Ile | |
| | | | 405 | | | | | 410 | | | | | 415 | | | |

| GTA | GGT | GGT | TTT | TTA | GGT | GGA | GGT | AGT | CTA | ACG | GAG | TAT | CTT | AGC | CTT | 1411 |
|---|---|---|---|---|---|---|---|---|---|---|---|---|---|---|---|---|
| Val | Gly | Gly | Phe | Leu | Gly | Gly | Gly | Ser | Leu | Thr | Glu | Tyr | Leu | Ser | Leu | |
| | | 420 | | | | | 425 | | | | | 430 | | | | |

| AAA | GAA | TAT | CAG | TCA | GAC | AGG | CTT | AAT | GCA | AGT | CAA | TTT | AAT | TAT | GAA | 1459 |
|---|---|---|---|---|---|---|---|---|---|---|---|---|---|---|---|---|
| Lys | Glu | Tyr | Gln | Ser | Asp | Arg | Leu | Asn | Ala | Ser | Gln | Phe | Asn | Tyr | Glu | |
| | 435 | | | | | 440 | | | | | 445 | | | | | |

| AGA | CGT | GTT | GGT | GAA | GGG | TAT | TAT | TAC | CAT | AGT | TTT | TCT | GAA | AGG | AAA | 1507 |
|---|---|---|---|---|---|---|---|---|---|---|---|---|---|---|---|---|
| Arg | Arg | Val | Gly | Glu | Gly | Tyr | Tyr | Tyr | His | Ser | Phe | Ser | Glu | Arg | Lys | |
| 450 | | | | | 455 | | | | | 460 | | | | | 465 | |

| ACT | GCT | GAA | ATG | CCG | AAC | AGA | GCA | CTT | ATT | AAG | AAA | CAA | TTA | GAA | GGC | 1555 |
|---|---|---|---|---|---|---|---|---|---|---|---|---|---|---|---|---|
| Thr | Ala | Glu | Met | Pro | Asn | Arg | Ala | Leu | Ile | Lys | Lys | Gln | Leu | Glu | Gly | |
| | | | | 470 | | | | | 475 | | | | | 480 | | |

| CTA | TTT | AAG | GGA | AAA | GAA | GGT | AAA | TGG | TTT | AAG | TCT | ATT | TTA | GAA | AAA | 1603 |
|---|---|---|---|---|---|---|---|---|---|---|---|---|---|---|---|---|
| Leu | Phe | Lys | Gly | Lys | Glu | Gly | Lys | Trp | Phe | Lys | Ser | Ile | Leu | Glu | Lys | |
| | | | 485 | | | | | 490 | | | | | 495 | | | |

| TTA | TCA | CTT | ACA | GAT | GAT | TAT | CAA | AAA | GCA | AAA | GAA | GAA | GCT | ATT | TTG | 1651 |
|---|---|---|---|---|---|---|---|---|---|---|---|---|---|---|---|---|
| Leu | Ser | Leu | Thr | Asp | Asp | Tyr | Gln | Lys | Ala | Lys | Glu | Glu | Ala | Ile | Leu | |
| | | 500 | | | | | 505 | | | | | 510 | | | | |

| AAA | GTG | CTT | GAT | TAC | TTC | TTT | TAC | AAA | AGA | GAC | TAT | ATT | TAC | TAC | AAT | 1699 |
|---|---|---|---|---|---|---|---|---|---|---|---|---|---|---|---|---|
| Lys | Val | Leu | Asp | Tyr | Phe | Phe | Tyr | Lys | Arg | Asp | Tyr | Ile | Tyr | Tyr | Asn | |
| | 515 | | | | | 520 | | | | | 525 | | | | | |

| CAC | AAT | CTC | TCA | GCA | ATA | GCT | GAA | GCC | AAA | ATG | GCT | CAA | CAA | GAG | GGG | 1747 |
|---|---|---|---|---|---|---|---|---|---|---|---|---|---|---|---|---|
| His | Asn | Leu | Ser | Ala | Ile | Ala | Glu | Ala | Lys | Met | Ala | Gln | Gln | Glu | Gly | |
| 530 | | | | | 535 | | | | | 540 | | | | | 545 | |

| GTC | ACC | TTC | TAT | TCC | GTT | GAT | GTT | ACT | GAT | TTC | AAC | TCA | GCT | TCT | AAA | 1795 |
|---|---|---|---|---|---|---|---|---|---|---|---|---|---|---|---|---|
| Val | Thr | Phe | Tyr | Ser | Val | Asp | Val | Thr | Asp | Phe | Asn | Ser | Ala | Ser | Lys | |
| | | | | 550 | | | | | 555 | | | | | 560 | | |

| AGA | GCA | AAG | CGA | CAA | GTA | AAA | AGT | GAA | GAG | GAT | AAG | AAA | AAA | GCA | AAA | 1843 |
|---|---|---|---|---|---|---|---|---|---|---|---|---|---|---|---|---|
| Arg | Ala | Lys | Arg | Gln | Val | Lys | Ser | Glu | Glu | Asp | Lys | Lys | Lys | Ala | Lys | |
| | | | 565 | | | | | 570 | | | | | 575 | | | |

| GAG | AAG | GAG | AAC | ATT | GAA | AAA | AAA | CGT | GAC | GAA | AAG | TTT | GAT | AAT | TAC | 1891 |
|---|---|---|---|---|---|---|---|---|---|---|---|---|---|---|---|---|
| Glu | Lys | Glu | Asn | Ile | Glu | Lys | Lys | Arg | Asp | Glu | Lys | Phe | Asp | Asn | Tyr | |
| | | 580 | | | | | 585 | | | | | 590 | | | | |

| TTA | AAA | CAA | ATG | TCT | GAA | GGC | GGT | AAA | GAA | TTT | TTT | AAC | GAT | GTG | GAT | 1939 |
|---|---|---|---|---|---|---|---|---|---|---|---|---|---|---|---|---|
| Leu | Lys | Gln | Met | Ser | Glu | Gly | Gly | Lys | Glu | Phe | Phe | Asn | Asp | Val | Asp | |
| | 595 | | | | | 600 | | | | | 605 | | | | | |

| AAG | GCA | GAG | AAT | TTC | AAA | GAT | ACC | CTA | ACC | AGT | GTG | ACA | GTG | ACA | GAG | 1987 |

|  |  |  |  |  |  |  |  |  |  |  |  |  |  |  |  |
|---|---|---|---|---|---|---|---|---|---|---|---|---|---|---|---|
| Lys<br>610 | Ala | Glu | Asn | Phe<br>615 | Lys | Asp | Thr | Leu | Thr<br>620 | Ser | Val | Thr | Val | Thr<br>625 | Glu |

| ACT | TTT | GGG | AAC | AAC | GTG | TCT | GTT | GAG | AGT | GGT | TCA | TGG | AAA | ACT | TCA | 2035 |
|---|---|---|---|---|---|---|---|---|---|---|---|---|---|---|---|---|
| Thr | Phe | Gly | Asn<br>630 | Asn | Val | Ser | Val | Glu | Ser<br>635 | Gly | Ser | Trp | Lys | Thr<br>640 | Ser |  |
| CTA | GGT | AGT | AAT | AGT | GGT | TCA | AGT | AGC | AGA | GAG | GTT | TCC | TAT | AAA | GGA | 2083 |
| Leu | Gly | Ser | Asn<br>645 | Ser | Gly | Ser | Ser | Ser<br>650 | Arg | Glu | Val | Ser | Tyr<br>655 | Lys | Gly |  |
| CGG | GAT | AGT | GGA | AGT | CTA | TTT | TCA | CTT | TTC | GGT | AGT | ACC | AAA | GAA | AGT | 2131 |
| Arg | Asp | Ser<br>660 | Gly | Ser | Leu | Phe | Ser<br>665 | Leu | Phe | Gly | Ser | Thr<br>670 | Lys | Glu | Ser |  |
| CTC | ACT | TGG | ACT | ATT | TCC | AAA | GAC | CAG | TTG | AAA | CAA | GCC | TTT | GAA | GAG | 2179 |
| Leu | Thr<br>675 | Trp | Thr | Ile | Ser | Lys<br>680 | Asp | Gln | Leu | Lys | Gln<br>685 | Ala | Phe | Glu | Glu |  |
| GGT | AAG | CCG | CTA | ACC | CTC | ACC | TAT | AAG | CTG | AAA | GTT | GAT | AAA | GAT | AAA | 2227 |
| Gly<br>690 | Lys | Pro | Leu | Thr<br>695 | Leu | Thr | Tyr | Lys | Leu<br>700 | Lys | Val | Asp | Lys | Asp<br>705 | Lys |  |
| TTT | AGA | GAA | ACT | CTT | AAA | AAG | CAA | CAA | GAA | TCT | CGT | CGT | ATA | AAG | AAA | 2275 |
| Phe | Arg | Glu | Thr | Leu<br>710 | Lys | Lys | Gln | Gln | Glu<br>715 | Ser | Arg | Arg | Ile | Lys<br>720 | Lys |  |
| CGA | GCA | GCA | TCT | TCG | GAA | AGT | GAG | AAC | ACT | GTC | ACA | GAA | ACA | ATT | ATT | 2323 |
| Arg | Ala | Ala | Ser<br>725 | Ser | Glu | Ser | Glu<br>730 | Asn | Thr | Val | Thr | Glu<br>735 | Thr | Ile | Ile |  |
| TCA | AAT | AAG | ATT | TCT | TAC | AAG | ATT | AAT | AAT | GGT | AAG | GAT | ACG | AAT | AAC | 2371 |
| Ser | Asn | Lys<br>740 | Ile | Ser | Tyr | Lys | Ile<br>745 | Asn | Asn | Gly | Lys | Asp<br>750 | Thr | Asn | Asn |  |
| AAT | AAG | TTG | GAA | GAA | GTT | AAA | ATG | TCT | TAC | AGC | AAG | TTC | AAA | ATG | CCT | 2419 |
| Asn | Lys<br>755 | Leu | Glu | Glu | Val<br>760 | Lys | Met | Ser | Tyr | Ser<br>765 | Lys | Phe | Lys | Met | Pro |  |
| ATA | CCA | GAA | CTT | GAT | ATA | GAA | GTT | GTA | GTA | CCA | AAA | GTA | CCA | GAA | AAA | 2467 |
| Ile<br>770 | Pro | Glu | Leu | Asp | Ile<br>775 | Glu | Val | Val | Val | Pro<br>780 | Lys | Val | Pro | Glu | Lys<br>785 |  |
| CCA | CTG | GTA | GAA | CCA | ATG | ACG | CCT | CTA | TAT | CCT | GCA | ATT | CCT | AAT | TAC | 2515 |
| Pro | Leu | Val | Glu | Pro<br>790 | Met | Thr | Pro | Leu | Tyr<br>795 | Pro | Ala | Ile | Pro | Asn<br>800 | Tyr |  |
| CCT | ACT | CCT | CAA | CTT | CCA | AAA | GAT | GAA | GAT | CTG | GAG | ATT | AGT | GGA | GGT | 2563 |
| Pro | Thr | Pro | Gln<br>805 | Leu | Pro | Lys | Asp | Glu<br>810 | Asp | Leu | Glu | Ile | Ser<br>815 | Gly | Gly |  |
| CAT | GGA | CCG | ATT | GTC | GAT | ATC | GTC | GAA | GAT | ACT | GGT | ACA | GGT | GTT | GAG | 2611 |
| His | Gly | Pro<br>820 | Ile | Val | Asp | Ile | Val<br>825 | Glu | Asp | Thr | Gly | Thr<br>830 | Gly | Val | Glu |  |
| GGC | GGC | GCT | CAA | AAC | GGC | GTG | GTT | TCA | ACT | CAG | GAA | AAT | AAA | GAT | CCA | 2659 |
| Gly | Gly | Ala<br>835 | Gln | Asn | Gly | Val<br>840 | Val | Ser | Thr | Gln | Glu<br>845 | Asn | Lys | Asp | Pro |  |
| ATC | GTT | GAC | ATC | ACC | GAA | GAT | ACC | CAA | CCA | GGT | ATG | TCA | GGC | TCA | AAT | 2707 |
| Ile<br>850 | Val | Asp | Ile | Thr | Glu<br>855 | Asp | Thr | Gln | Pro | Gly<br>860 | Met | Ser | Gly | Ser | Asn<br>865 |  |
| GAC | GCG | ACA | GTT | GTC | GAG | GAA | GAC | ACA | ACA | CCT | CAA | CGC | CCA | GAT | GTC | 2755 |
| Asp | Ala | Thr | Val | Val<br>870 | Glu | Glu | Asp | Thr | Thr<br>875 | Pro | Gln | Arg | Pro | Asp<br>880 | Val |  |
| CTT | GTA | GGT | GGT | CAA | AGT | GAT | CCA | ATC | GAT | ATC | ACT | GAA | GAT | ACC | CAA | 2803 |
| Leu | Val | Gly | Gly<br>885 | Gln | Ser | Asp | Pro | Ile<br>890 | Asp | Ile | Thr | Glu | Asp<br>895 | Thr | Gln |  |
| CCA | GGC | ATG | TCA | GGC | TCA | AAT | GAC | GCG | ACA | GTT | GTC | GAG | GAA | GAC | ACA | 2851 |
| Pro | Gly | Met<br>900 | Ser | Gly | Ser | Asn | Asp<br>905 | Ala | Thr | Val | Val | Glu<br>910 | Glu | Asp | Thr |  |
| GTA | CCT | AAA | CGT | CCA | GAT | ATC | CTT | GTT | GGC | GGT | CAA | AGT | GAT | CCA | ATC | 2899 |
| Val | Pro<br>915 | Lys | Arg | Pro | Asp | Ile<br>920 | Leu | Val | Gly | Gly | Gln<br>925 | Ser | Asp | Pro | Ile |  |
| GAT | ATC | ACC | GAA | GAT | ACC | CAA | CCA | GGT | ATG | TCA | GGC | TCA | AAT | GAC | GCT | 2947 |

|   |   |   |   |   |   |   |   |   |   |   |   |   |   |   |   |      |
|---|---|---|---|---|---|---|---|---|---|---|---|---|---|---|---|------|
| Asp | Ile | Thr | Glu | Asp | Thr | Gln | Pro | Gly | Met | Ser | Gly | Ser | Asn | Asp | Ala | |
| 930 | | | | | 935 | | | | 940 | | | | | | 945 | |

```
ACT GTT ATC GAA GAA GAT ACG AAA CCA AAA CGC TTC TTC CAC TTT GAT        2995
Thr Val Ile Glu Glu Asp Thr Lys Pro Lys Arg Phe Phe His Phe Asp
                950                 955                 960

AAC GAG CCA CAA GCA CCA GAA AAA CCT AAA GAG CAA CCA TCT CTC AGC        3043
Asn Glu Pro Gln Ala Pro Glu Lys Pro Lys Glu Gln Pro Ser Leu Ser
            965                 970                 975

TTA CCA CAA GCT CCA GTC TAT AAG GCA GCT CAT CAC TTG CCT GCA TCT        3091
Leu Pro Gln Ala Pro Val Tyr Lys Ala Ala His His Leu Pro Ala Ser
            980                 985                 990

GGA GAC AAA CGT GAA GCA TCC TTT ACA ATT GTT GCT CTA ACA ATT ATT        3139
Gly Asp Lys Arg Glu Ala Ser Phe Thr Ile Val Ala Leu Thr Ile Ile
        995                1000                1005

GGA GCT GCA GGT TTG CTC AGC AAA AAA CGT CGC GAC ACC GAA GAA AAC        3187
Gly Ala Ala Gly Leu Leu Ser Lys Lys Arg Arg Asp Thr Glu Glu Asn
1010                1015                1020                1025

TAACTCTCGT TAGTCTAGCG ACCCTAAGCC TTTGGCTTTA AGAATTTCTC ATT             3240
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:3:

```
Leu Pro Ala Ser Gly Asp
1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:4:

```
Ser Pro Xaa Thr Gly Xaa
1               5
```

( 2 ) INFORMATION FOR SEQ ID NO:5:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: unknown ( i i ) MOLECULE TYPE: peptide ( v ) FRAGMENT TYPE: C-terminal ( v i ) ORIGINAL SOURCE:
        ( A ) ORGANISM: Streptococcus pyogenes
        ( B ) STRAIN: D734
        ( C ) INDIVIDUAL ISOLATE: 22

( v i i ) IMMEDIATE SOURCE:
        ( B ) CLONE: sAU3a ( x i ) SEQUENCE DESCRIPTION: SEQ ID NO:5:

Gln Glu Asn Lys Asp Pro Ile Val Asp Ile Thr Glu Asp Thr Gln Pro
1               5                   10                  15

Gly Met Ser Gly Ser Asn Asp Ala Thr Val Val Glu Glu Asp Thr Thr
            20                  25                  30

Pro Gln Arg Pro Asp Val Leu Val Gly Gly Gln Ser Asp Pro Ile Asp
        35                  40                  45

Ile Thr Glu Asp Thr Gln Pro Ser Met Ser Gly Ser Asn Asp Ala Thr
    50                  55                  60

Val Val Glu Glu Asp Val Thr Pro Gln Arg Pro Asp Ile Leu Val Gly
65                  70                  75                  80

Gly Gln Ser Asp Pro Ile Asp Ile Thr Glu Asp Thr Gln Pro Ser Met
                85                  90                  95

Ser Gly Ser Asn Asp Ala Thr Val Ile Glu Glu Asp Thr Lys Pro Lys
            100                 105                 110

Arg Phe Phe His Phe Asp Asn Glu
        115                 120

( 2 ) INFORMATION FOR SEQ ID NO:6:

( i ) SEQUENCE CHARACTERISTICS:
         ( A ) LENGTH: 39 amino acids
         ( B ) TYPE: amino acid
         ( C ) STRANDEDNESS: single
         ( D ) TOPOLOGY: unknown ( i i ) MOLECULE TYPE: peptide ( v i ) ORIGINAL SOURCE:
         ( A ) ORGANISM: Streptococcus pyogenes
         ( B ) STRAIN: D734
         ( C ) INDIVIDUAL ISOLATE: 22

( v i i ) IMMEDIATE SOURCE:
         ( B ) CLONE: sAU3a ( x i ) SEQUENCE DESCRIPTION: SEQ ID NO:6:

Val Val Glu Glu Asp Thr Thr Pro Gln Arg Pro Asp Val Leu Val Gly
1               5                   10                  15

Gly Gln Ser Asp Pro Ile Asp Ile Thr Glu Asp Thr Gln Pro Ser Met
            20                  25                  30

Ser Gly Ser Asn Asp Ala Thr
            35

( 2 ) INFORMATION FOR SEQ ID NO:7:

( i ) SEQUENCE CHARACTERISTICS:
         ( A ) LENGTH: 37 amino acids
         ( B ) TYPE: amino acid
         ( C ) STRANDEDNESS: single
         ( D ) TOPOLOGY: unknown ( i i ) MOLECULE TYPE: peptide ( v i ) ORIGINAL SOURCE:
         ( A ) ORGANISM: Streptococcus pyogenes
         ( B ) STRAIN: D734
         ( C ) INDIVIDUAL ISOLATE: 22

( v i i ) IMMEDIATE SOURCE:
         ( B ) CLONE: sAU3a ( x i ) SEQUENCE DESCRIPTION: SEQ ID NO:7:

Val Glu Thr Glu Asp Thr Lys Glu Pro Gly Val Leu Met Gly Gly Gln
1               5                   10                  15

```
Ser Glu Ser Val Glu Phe Thr Lys Asp Thr Gln Thr Gly Met Ser Gly
            20              25              30

Gln Thr Thr Pro Gln
        35
```

( 2 ) INFORMATION FOR SEQ ID NO:8:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: unknown ( i i ) MOLECULE TYPE: peptide ( v i ) ORIGINAL SOURCE:
    ( A ) ORGANISM: Streptococcus pyogenes
    ( B ) STRAIN: D734
    ( C ) INDIVIDUAL ISOLATE: 22

( v i i ) IMMEDIATE SOURCE:
    ( B ) CLONE: sAU3a ( x i ) SEQUENCE DESCRIPTION: SEQ ID NO:8:

```
Ile Ile Glu Glu Asp Thr Asn Lys Asp Lys Pro Ser Tyr Gln Phe Gly
1               5                   10                  15

Gly His Asn Ser Val Asp Phe Glu Glu Asp Thr Leu Pro Lys Val Ser
            20              25              30

Gly Gln Asn Glu Gly Gln
        35
```

( 2 ) INFORMATION FOR SEQ ID NO:9:

( i ) SEQUENCE CHARACTERISTICS:
    ( A ) LENGTH: 51 amino acids
    ( B ) TYPE: amino acid
    ( C ) STRANDEDNESS: single
    ( D ) TOPOLOGY: unknown ( i i ) MOLECULE TYPE: peptide ( v ) FRAGMENT TYPE: C-terminal ( v i ) ORIGINAL SOURCE:
    ( A ) ORGANISM: Streptococcus pyogenes
    ( B ) STRAIN: d734
    ( C ) INDIVIDUAL ISOLATE: 22

( v i i ) IMMEDIATE SOURCE:
    ( B ) CLONE: sAU3a ( x i ) SEQUENCE DESCRIPTION: SEQ ID NO:9:

```
Ser Leu Ser Leu Pro Gln Ala Pro Val Tyr Lys Ala Ala His His Leu
1               5                   10                  15

Pro Ala Ser Gly Asp Lys Arg Glu Ala Ser Phe Thr Ile Val Ala Leu
            20              25              30

Thr Ile Ile Gly Ala Ala Gly Leu Leu Ser Lys Lys Arg Arg Asp Thr
            35              40              45

Glu Glu Asn
    50
```

( 2 ) INFORMATION FOR SEQ ID NO:10:

( i ) SEQUENCE CHARACTERISTICS:
    ( A ) LENGTH: 50 amino acids
    ( B ) TYPE: amino acid
    ( C ) STRANDEDNESS: single
    ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
    ( A ) ORGANISM: Streptococcus pyogenes ( x i ) SEQUENCE DESCRIPTION: SEQ ID NO:10:

```
Lys Pro Asn Gln Asn Lys Ala Pro Met Lys Glu Thr Lys Arg Gln Leu
 1               5                  10                  15

Pro Ser Thr Gly Glu Thr Ala Asn Pro Phe Phe Thr Ala Ala Ala Leu
                20                  25                  30

Thr Val Met Ala Thr Ala Gly Val Ala Ala Val Val Lys Arg Lys Glu
            35                  40                  45

Glu Asn
    50
```

( 2 ) INFORMATION FOR SEQ ID NO:11:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( x i ) SEQUENCE DESCRIPTION: SEQ ID NO:11:

```
Lys Pro Asn Gln Asn Lys Ala Pro Met Lys Glu Thr Lys Arg Gln Leu
 1               5                  10                  15

Pro Ser Thr Gly Glu Thr Ala Asn Pro Phe Phe Thr Ala Ala Ala Leu
                20                  25                  30

Thr Val Met Ala Thr Ala Gly Val Ala Ala Val Val Lys Arg Lys Glu
            35                  40                  45

Glu Asn
    50
```

( 2 ) INFORMATION FOR SEQ ID NO:12:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
    ( A ) ORGANISM: Streptococcus pyogenes ( x i ) SEQUENCE DESCRIPTION: SEQ ID NO:12:

```
Gln Ala Asn Arg Ser Arg Ser Ala Met Thr Gln Gln Lys Arg Thr Leu
 1               5                  10                  15

Pro Ser Thr Gly Glu Thr Ala Asn Pro Phe Phe Thr Ala Ala Ala Ala
                20                  25                  30

Thr Val Met Val Ser Ala Gly Met Leu Ala Leu Lys Arg Lys Glu Glu
            35                  40                  45
```

Asn ( 2 ) INFORMATION FOR SEQ ID NO:13:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
        ( A ) ORGANISM: Streptococcus pyogenes ( x i ) SEQUENCE DESCRIPTION: SEQ ID NO:13:

```
Gln Thr Ala Thr Arg Pro Ser Gln Asn Lys Gly Met Arg Ser Gln Leu
 1               5                  10                  15

Pro Ser Thr Gly Glu Ala Ala Asn Pro Phe Phe Thr Ala Ala Ala Ala
             20                  25                  30

Thr Val Met Val Ser Ala Gly Met Leu Ala Leu Lys Arg Lys Glu Glu
             35                  40                  45

Asn
```

( 2 ) INFORMATION FOR SEQ ID NO:14:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
        ( A ) ORGANISM: Group G Streptococci ( x i ) SEQUENCE DESCRIPTION: SEQ ID NO:14:

```
Lys Lys Pro Glu Ala Lys Lys Asp Asp Ala Lys Lys Ala Glu Thr Leu
 1               5                  10                  15

Pro Thr Thr Gly Glu Gly Ser Asn Pro Phe Phe Thr Ala Ala Ala Leu
             20                  25                  30

Ala Val Met Ala Gly Ala Gly Ala Leu Ala Val Ala Ser Lys Arg Lys
             35                  40                  45

Glu Asp
     50
```

( 2 ) INFORMATION FOR SEQ ID NO:15:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
    ( A ) ORGANISM: Streptococcus mutans ( x i ) SEQUENCE DESCRIPTION: SEQ ID NO:15:

```
Thr Thr Thr Ser Lys Gln Val Thr Lys Gln Lys Ala Lys Phe Val Leu
1               5                   10                  15
Pro Ser Thr Gly Glu Gln Ala Gly Leu Leu Leu Thr Thr Val Gly Leu
            20                  25                  30
Val Ile Val Ala Val Ala Gly Val Tyr Phe Tyr Arg Thr Arg Arg
        35                  40                  45
```

( 2 ) INFORMATION FOR SEQ ID NO:16:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
        ( A ) ORGANISM: Staphylococcus aureus ( x i ) SEQUENCE DESCRIPTION: SEQ ID NO:16:

```
Lys Lys Gln Pro Ala Asn His Ala Asp Ala Asn Lys Ala Gln Ala Leu
1               5                   10                  15
Pro Glu Thr Gly Glu Glu Asn Pro Leu Ile Gly Thr Thr Val Phe Gly
            20                  25                  30
Gly Leu Ser Leu Ala Leu Gly Ala Ala Leu Leu Ala Gly Arg Arg Arg
        35                  40                  45
Glu Leu
    50
```

( 2 ) INFORMATION FOR SEQ ID NO:17:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
        ( A ) ORGANISM: Staphylococcus aureus ( x i ) SEQUENCE DESCRIPTION: SEQ ID NO:17:

```
Lys Ala Val Ala Pro Thr Lys Lys Pro Gln Ser Lys Lys Ser Glu Leu
1               5                   10                  15
Pro Glu Thr Gly Gly Glu Glu Ser Thr Asn Lys Gly Met Leu Phe Gly
            20                  25                  30
Gly Leu Phe Ser Ile Leu Gly Leu Ala Leu Leu Arg Arg Asn Lys Lys
        35                  40                  45
Asn His Lys Ala
    50
```

( 2 ) INFORMATION FOR SEQ ID NO:18:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( v i ) ORIGINAL SOURCE:
        ( A ) ORGANISM: Streptococcus pyogenes ( x i ) SEQUENCE DESCRIPTION: SEQ ID NO:18:

```
Ser Ser Lys Arg Ala Leu Ala Thr Lys Ala Ser Thr Arg Asp Gln Leu
 1               5                  10                  15
Pro Thr Thr Asn Asp Lys Asp Thr Asn Arg Leu His Leu Leu Lys Leu
            20                  25                  30
Val Met Thr Thr Phe Phe Phe Gly Leu Val Ala His Ile Phe Lys Thr
        35                  40                  45
Lys Arg Gln Lys Glu Thr Lys Lys
 50                  55
```

( 2 ) INFORMATION FOR SEQ ID NO:19:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( v ) FRAGMENT TYPE: C-terminal ( x i ) SEQUENCE DESCRIPTION: SEQ ID NO:19:

```
Val Glu Glu Asn Arg Glu Lys Pro Thr Lys Asn Ile Thr Pro Ile Leu
 1               5                  10                  15
Pro Ala Thr Gly Asp Asp Ile Glu Asn Val Leu Ala Phe Leu Gly Ile
            20                  25                  30
Leu Ile Leu Ser Val Leu Pro Ile Phe Ser Leu Leu Lys Lys Gln Thr
        35                  40                  45
Lys Gln
 50
```

( 2 ) INFORMATION FOR SEQ ID NO:20:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Streptococcus pyogenes
        ( B ) STRAIN: D734
        ( C ) INDIVIDUAL ISOLATE: 22

```
      ( v i i ) IMMEDIATE SOURCE:
              ( B ) CLONE: sAU3a ( x i ) SEQUENCE DESCRIPTION: SEQ ID NO:20:

GATCATTAAT  TTTTATCTCA  CCAAAAAACT  GATTTTAGAA  ACGAAAAAGC  ATGGTGTATA        60

ATAAAGTTC                                                                    69

( 2 ) INFORMATION FOR SEQ ID NO:21:

( i ) SEQUENCE CHARACTERISTICS:
              ( A ) LENGTH: 71 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

AGGTCACAAA  CTAAACAACT  CTTAAAAAGC  TGACCTTTAC  TAATAATCGT  CTTTTTTTA        60

TAATAAAGAT  G                                                                71

( 2 ) INFORMATION FOR SEQ ID NO:22:

( i ) SEQUENCE CHARACTERISTICS:
              ( A ) LENGTH: 24 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

CCCAAGCTTC  AGGAAAATAA  AGAT                                                 24

( 2 ) INFORMATION FOR SEQ ID NO:23:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

CGGGATCCGC  TCGTTATCAA  AGTGG                                                25
```